United States Patent
Bari et al.

(10) Patent No.: US 11,957,715 B2
(45) Date of Patent: Apr. 16, 2024

(54) METHOD FOR NK CELL TRANSDUCTION

(71) Applicant: MILTENYI BIOTEC B.V. & CO. KG, Bergisch Gladbach (DE)

(72) Inventors: Rafijul Bari, Gaithersburg, MD (US); Markus Granzin, Germering (DE); Wing Leung, Boston, MA (US); Nina Moker, Cologne (DE); Volker Huppert, Kurten (DE)

(73) Assignee: MILTENYI BIOTEC B.V. & CO. KG, Bergisch Gladbach (DE)

( * ) Notice: Subject to any disclaimer, the term of this patent is extended or adjusted under 35 U.S.C. 154(b) by 709 days.

(21) Appl. No.: 16/954,912

(22) PCT Filed: Dec. 19, 2018

(86) PCT No.: PCT/EP2018/085890
§ 371 (c)(1),
(2) Date: Jun. 17, 2020

(87) PCT Pub. No.: WO2019/121945
PCT Pub. Date: Jun. 27, 2019

(65) Prior Publication Data
US 2020/0390812 A1  Dec. 17, 2020

Related U.S. Application Data

(60) Provisional application No. 62/607,944, filed on Dec. 20, 2017.

(51) Int. Cl.
| | | |
|---|---|---|
| *A61K 35/17* | (2015.01) | |
| *C07K 14/54* | (2006.01) | |
| *C07K 14/545* | (2006.01) | |
| *C07K 14/55* | (2006.01) | |
| *C12N 15/867* | (2006.01) | |

(52) U.S. Cl.
CPC .......... *A61K 35/17* (2013.01); *C07K 14/5443* (2013.01); *C07K 14/545* (2013.01); *C07K 14/55* (2013.01); *C12N 15/867* (2013.01); *C07K 2319/85* (2013.01); *C12N 2740/13044* (2013.01)

(58) Field of Classification Search
CPC .......... A61K 35/17; C12N 2740/13044; C12N 15/867
See application file for complete search history.

(56) References Cited

U.S. PATENT DOCUMENTS

2014/0235700 A1 * 8/2014 Girard-Gagnepain ........................ C07K 14/005
435/456

FOREIGN PATENT DOCUMENTS

WO    2013045639 A1    4/2013

OTHER PUBLICATIONS

Girard-Gagnepain et al. Blood. 2014; 124(8):1221-1231 (Year: 2014).*
Glienke et al. Advantages and applications of CAR-expressing natural killer cells. Frontiers in Pharmacology, 2015; 6 (12):21 (Year: 2015).*
Aiuti et al., Gene Therapy for Immunodeficiency Due to Adenosine Deaminase Deficiency, The New England Journal of Medicine, vol. 360, No. 5, Jan. 29, 2009, pp. 447-458.
Aiuti et al., Ten Years of Gene Therapy for Primary Immune Deficiencies, American Society of Hematology, Newer Progress in Gene Therapy, 2009, pp. 682-689.
Childs et al., Bringing Natural Killer Cells to the Clinic: Ex Vivo Manipulation, Clinical Production and Applications of Natural Killercell Immunotherapy, American Society of Hematology, vol. 2013, No. 1, 2013, pp. 234-246.
Childs et al., Therapeutic Approaches to Enhance Natural Killer Cell Cytotoxicity Against Cancer: The Force Awakens, Nature Reviews, vol. 14, No. 7, Jul. 2015, pp. 487-498.
Colamartino et al., Baboon Retrovirus Envelope Pseudotyped Lentivectors Permit Robust Transduction of NK Cells and Represent and Improved Tool for Cancer Immunotherapy, Molecular Therapy May 1, 2018 Cell Press NLD, vol. 26, No. 5, May 1, 2018.
Costa et al., Baboon Envelope Pseudotyped Lentiviral Vectors: A Highly Efficient New Tool to Genetically Manipulate T-cell Acute Lymphoblastic Leukaemia-Initiating Cells, Leukemia, vol. 31, No. 4, Apr. 2017, pp. 977-980.
Girard-Gagnepain et al., Baboon Envelope Pseudotyped Lvs Outperform VSV-G-LVs for Gene Transfer into Early-Cytokine-Stimulated and Resting HSCs, Plenary Paper, Blood, vol. 124, No. 8, Aug. 21, 2014, pp. 1221-1231.
Glienke et al., Advantages and Applications of Car-Expressing Natural Killer Cells, Frontiers in Pharmacology vol. 6, No. 21, Feb. 12, 2010, 7 pages.
Klingemann, Are Natural Killer Cells Superior Car Drivers? Oncolmmunology, vol. 3, e28147, Feb. 2014, pp. e28147-1-e28147-4.
Leung, Infusions of Allogeneic Natural Killer Cells as Cancer Therapy, Clinical Cancer Research, vol. 20, No. 13, Jul. 1, 2014, pp. 3390-3400.

(Continued)

*Primary Examiner* — Vanessa L. Ford
*Assistant Examiner* — Sandra Dillahunt
(74) *Attorney, Agent, or Firm* — Kilpatrick Townsend & Stockton LLP

(57) ABSTRACT

The present invention discloses an in-vitro method for transferring biological material into activated NK cells with a pseudotyped retroviral vector particle or a virus-like particle thereof, comprising the steps a) activation of NK cells, and b) addition of said pseudotyped retroviral vector particle or virus-like particle thereof to said activated NK cells, wherein said pseudotyped retroviral vector particle or virus-like particle thereof comprises a modified baboon endogenous retrovirus (BaEV) envelope glycoprotein that is able of binding to and fusing with a hematopoietic cell membrane, thereby transferring biological material into said activated NK cells. Preferentially, the activating of NK cells is performed by the addition of a IL-1 family cytokine to the NK cells.

16 Claims, 12 Drawing Sheets

Specification includes a Sequence Listing.

(56) References Cited

OTHER PUBLICATIONS

Levy et al., Baboon Envelope Pseudotyped Lentiviral Vectors Efficiently Transduce Human B Cells and Allow Active Factor IX B Cell Secretion in vivo in NOD/SCID [gamma]c−/− Mice, Journal of Thrombosis and Haemostasis, vol. 14, No. 12, Dec. 2016, pp. 2478-2492.

Miller et al., Successful Adoptive Transfer and in Vivo Expansion of Human Haploidentical NK Cells in Patients with Cancer, Blood, vol. 105, No. 8, Apr. 15, 2005, pp. 3051-3057.

Montini et al., The Genotoxic Potential of Retroviral Vectors is Strongly Modulated by Vector Design and Integration Site Selection in a Mouse Model of HSC Gene Therapy, The Journal of Clinical Investigation, vol. 119, No. 4, Apr. 2009, pp. 964-975.

Papayannakos et al., Understanding Lentiviral Vector Chromatin Targeting: Working to Reduce Insertional Mutagenic Potential for Gene Therapy, Gene Therapy, vol. 20, Jun. 2013, pp. 581-588.

International Application No. PCT/EP2018/085890, International Search Report and Written Opinion dated Feb. 20, 2019, 10 pages.

Pillai et al., Tank Binding Kinase 1 is a Centrosome-Associated Kinase Necessary for Microtubule Dynamics and Mitosis, Nature Communications, vol. 6, Dec. 10, 2015, 14 pages.

Rubnitz et al., NKAML: A Pilot Study to Determine the Safety and Feasibility of Haploidentical Natural Killer Cell Transplantation in Childhood Acute Myeloid Leukemia, Journal of Clinical Oncology, vol. 28, No. 6, Feb. 20, 2010, pp. 955-959.

Schneider et al., A Tandem CD19/CD20 Car Lentiviral Vector Drives on-target and Off-Target Antigen Modulation in Leukemia Cell Lines, Journal for ImmunoTherapy of Cancer, vol. 5, No. 42, May 16, 2017, 17 pages.

Sutlu et al., Inhibition of Intracellular Antiviral Defense Mechanisms Augments Lentiviral Transduction of Human Natural Killer Cells: Implications for Gene Therapy, Human Gene Therapy, vol. 23, Oct. 2012, pp. 1090-1100.

\* cited by examiner

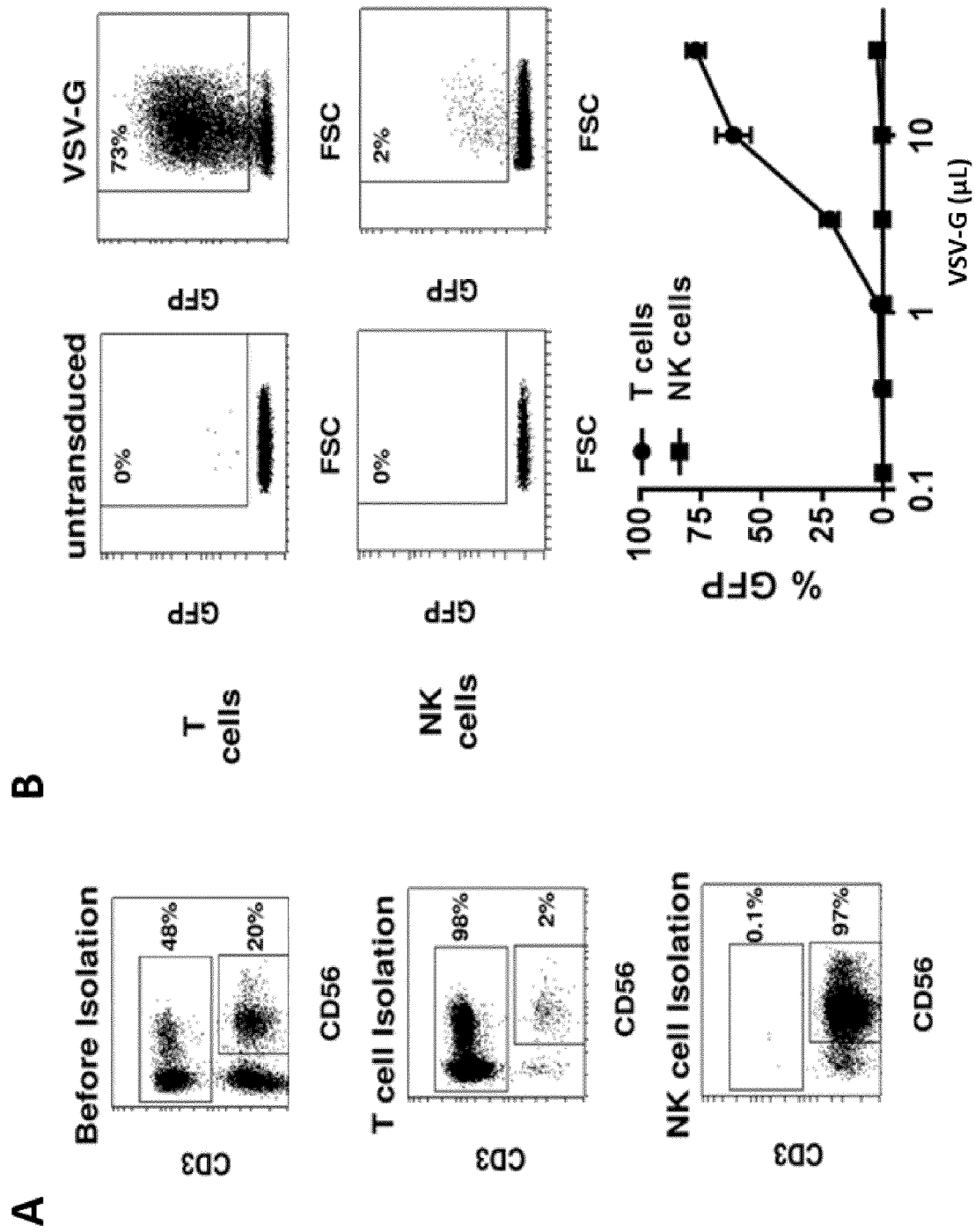
FIG 2 A-B

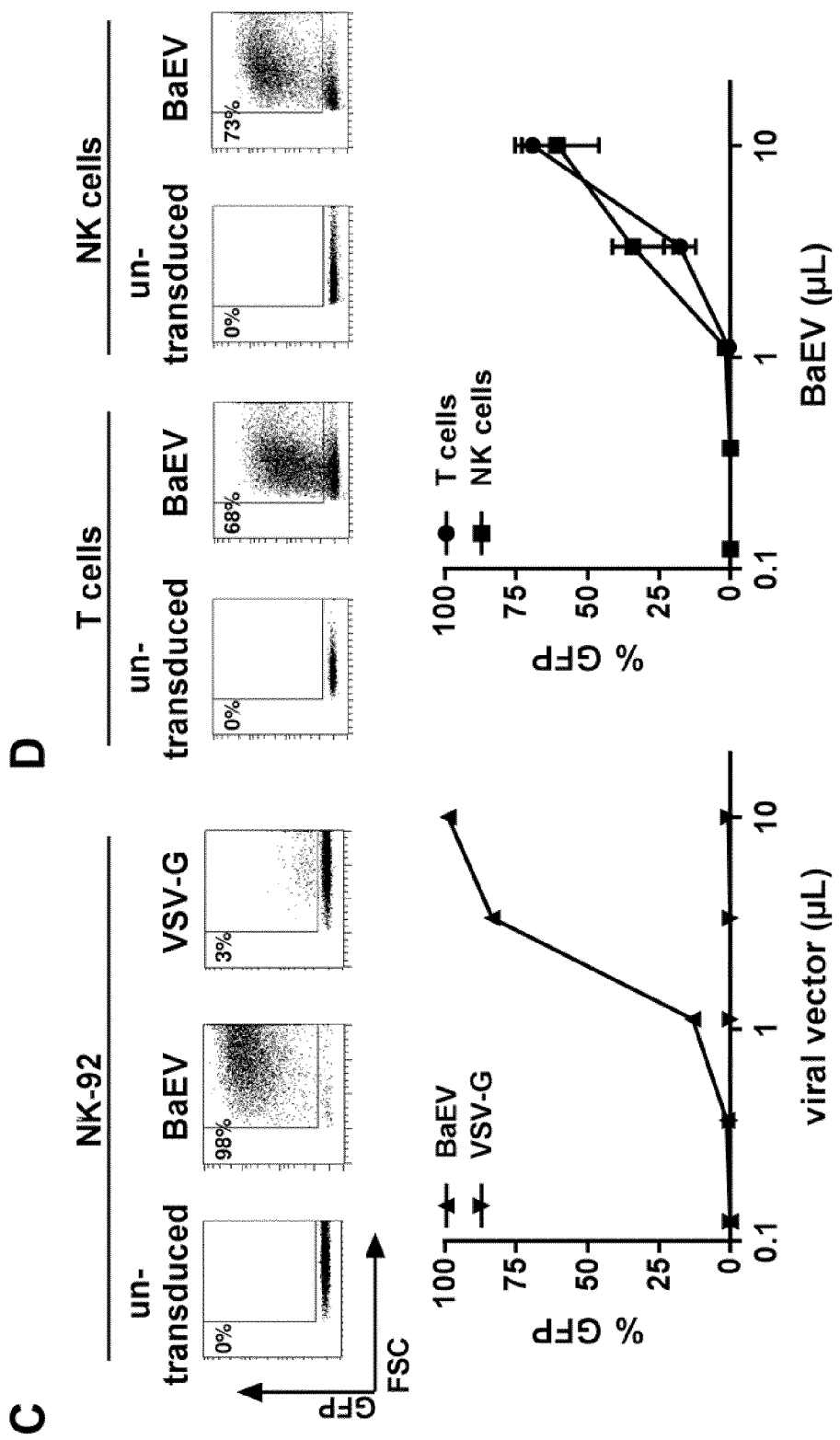
FIG 2 C-D

B

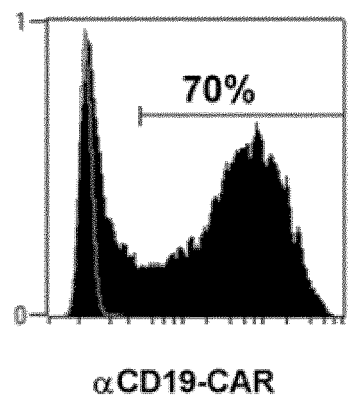
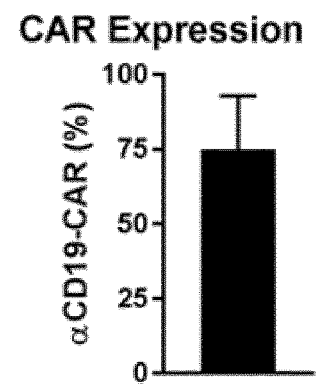
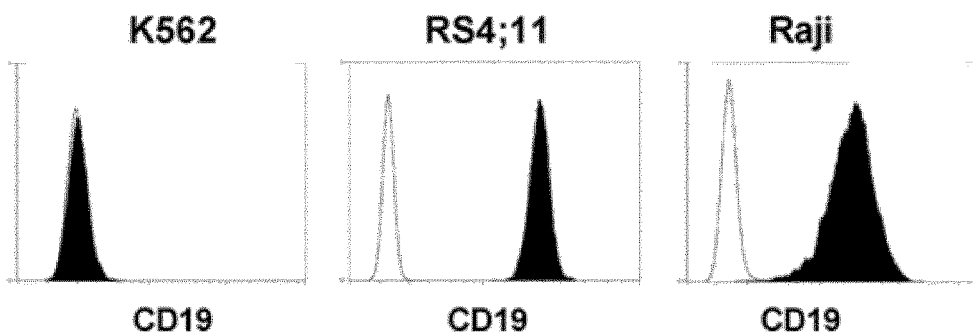
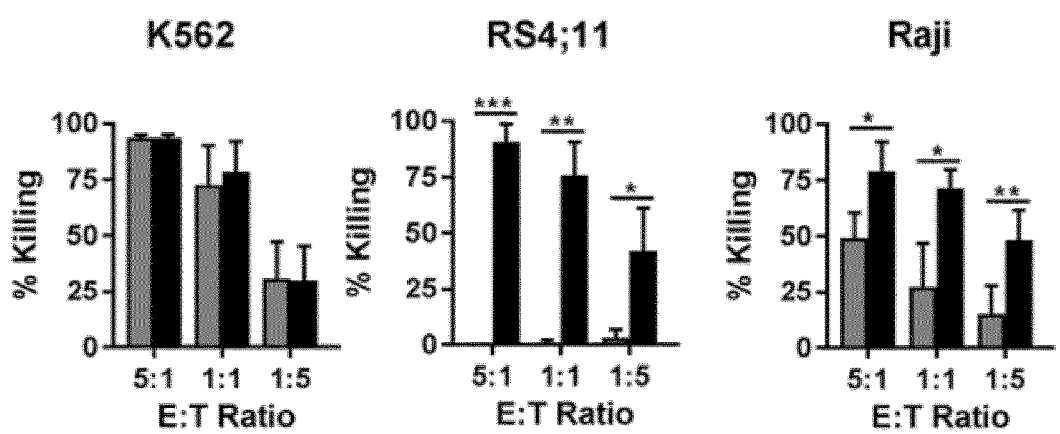
FIG 7 A-C

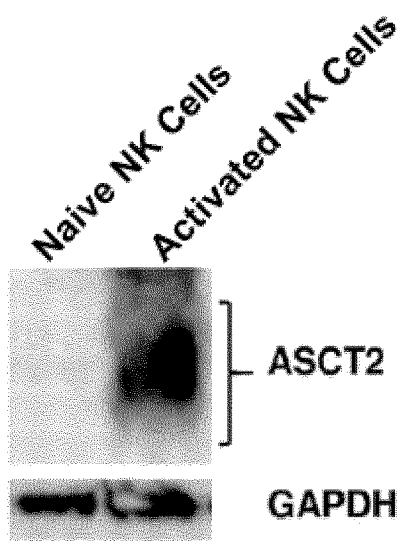
FIG 8
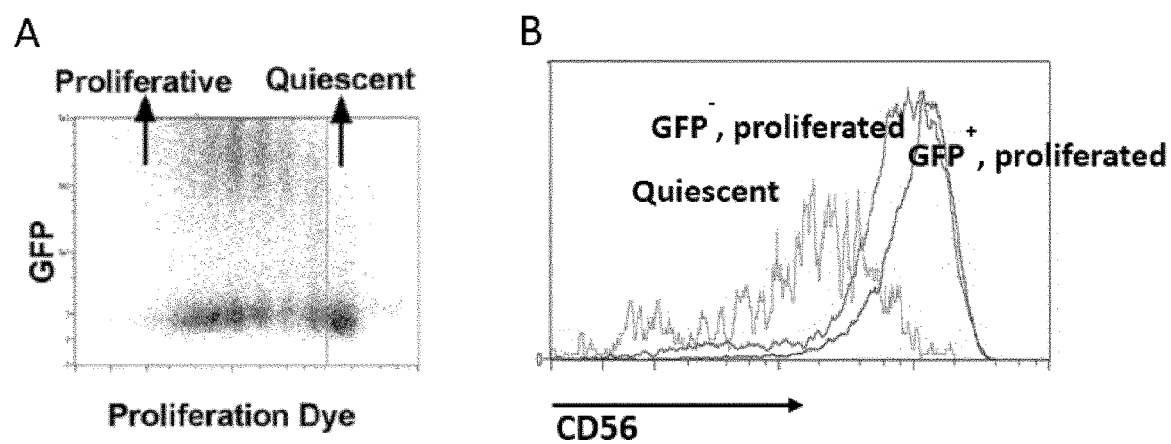
FIG 9 A-B

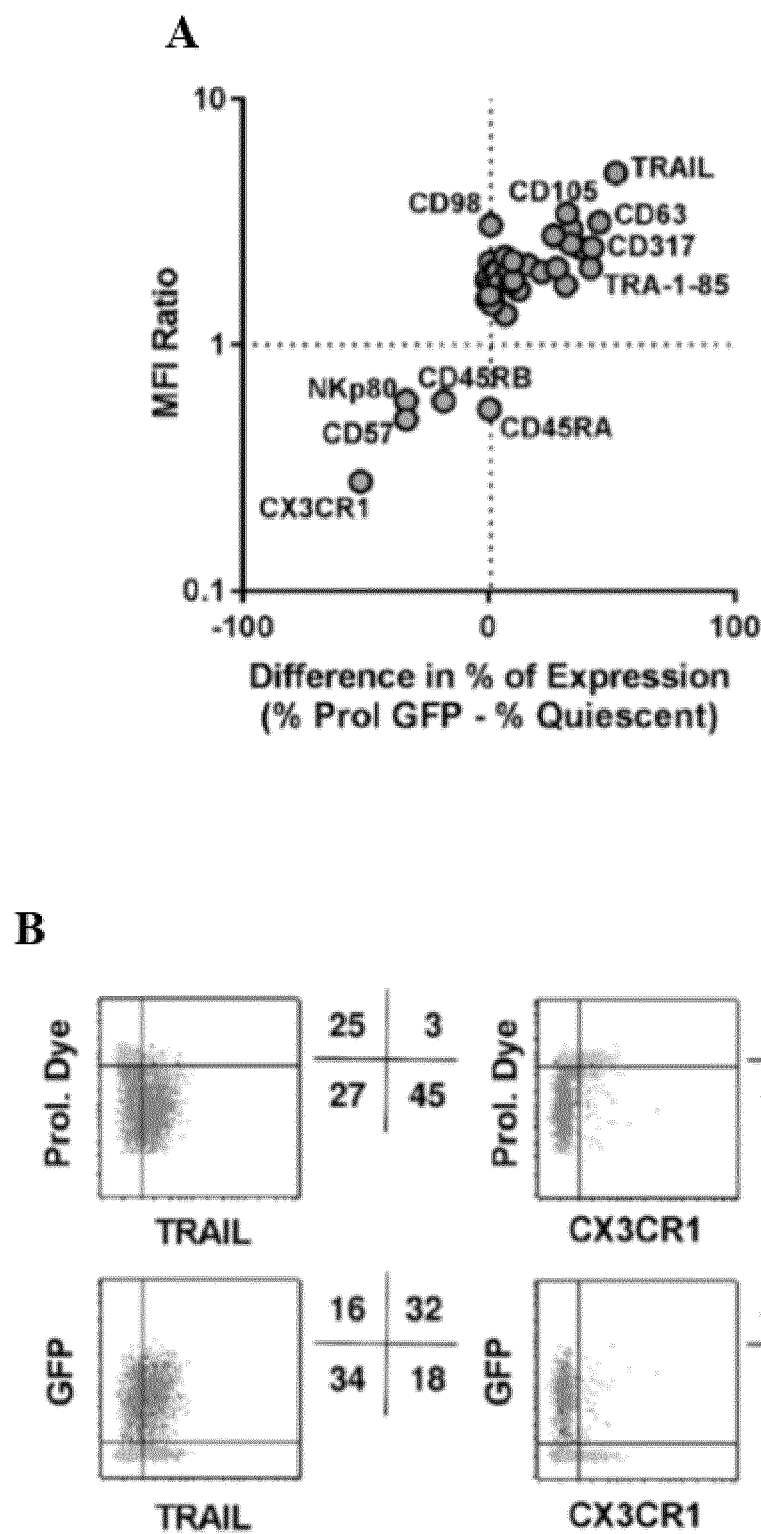
FIG 11 A-B

A
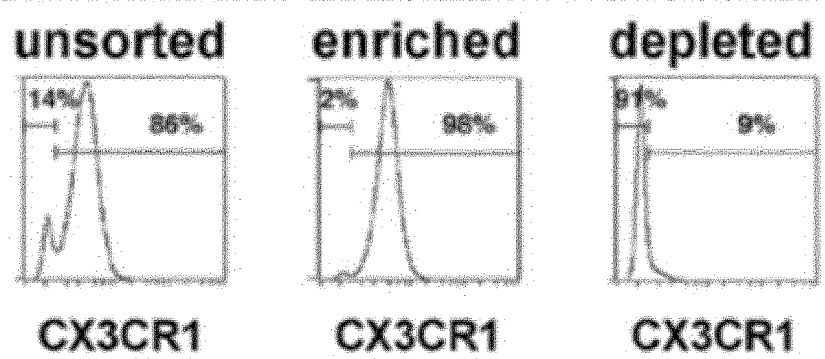
B
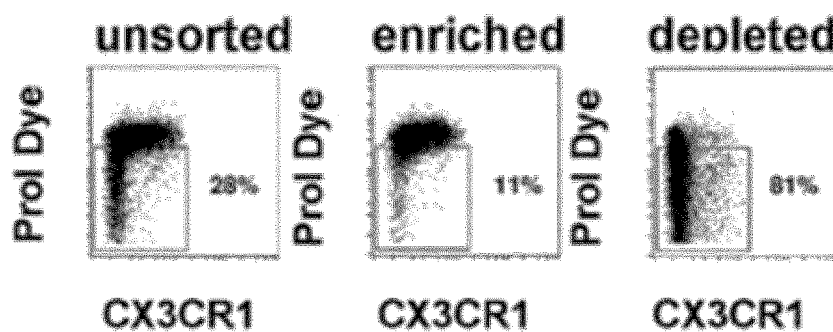
C
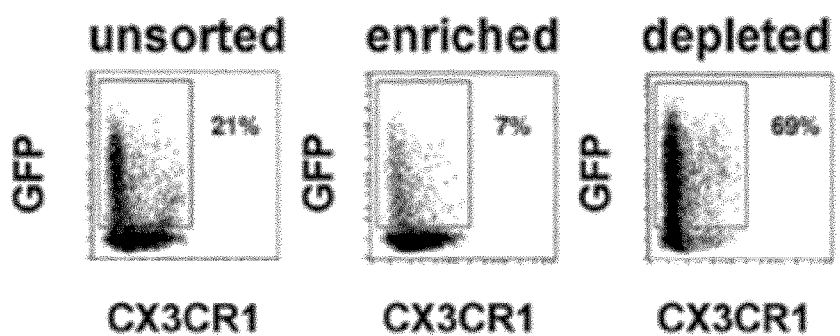
FIG 12 A-C

METHOD FOR NK CELL TRANSDUCTION

REFERENCE TO RELATED APPLICATIONS

This is the U.S. National Stage of international patent application PCT/EP2018/085890, filed on Dec. 19, 2018, and published on Jun. 27, 2019 with publication number WO 2019/121945. The PCT application claims the priority benefit of U.S. provisional patent application 62/607,944, filed Dec. 20, 2017. The PCT application is hereby incorporated herein by reference its entirety for all purposes.

FIELD OF THE INVENTION

The present invention generally relates to the field of transferring biological material into cells, in particular to transferring biological material into activated Natural Killer (NK) cells.

BACKGROUND OF THE INVENTION

Natural Killer cells (hereinafter also abbreviated as "NK cells") are a unique population of lymphocytes that are able to detect and destroy virus infected cells and malignantly degenerated cells, also known as tumor cells. Additionally, NK cells produce and secrete cytokines upon contact with tumor cells. These functional feature makes NK cells an attractive drug for treatment of cancer. Clinical trials have emphasized the potential of clinical use of NK cells (Miller et al. 2005; Rubnitz et al. 2010; Childs & Berg 2013).

Use of donor NK cells for patients ("allogeneic use") requires cell separation methods to separate wanted NK cell effects from non-wanted, contra-indicatory effects of non-NK cells, e.g. T cells. Those methods are well established (Leung 2014), and can be automated within closed, sterile systems (Apel et al. 2013).

Genetic manipulation is a promising strategy to further modify NK cell properties with a variety of clinical implications, e.g. in cancer treatment (Childs & Carlsten 2015). The use of chimeric antigen receptor (CAR) expressing immune cells for example is a promising treatment option for cancer, as shown in clinical trials with CAR T cells. CAR NK cells may be a good alternative to CAR T cells, however, genetic manipulation of primary NK cells represents a major technical challenge (Klingemann 2014).

Transfection approaches, such as electroporation, result in efficient transgene delivery, but the transgene expression is transient. Thus transfection of NK cells cannot be used for clinical applications when a durable effect is required. Moreover, transfection results in high rates of cell death, representing another major disadvantage.

On the other hand, viral vector based transduction of NK cells is an option for durable genetic modification. Retroviral transduction of NK cells is possible but require high virus titers, while the efficiency is still low (Suerth et al. 2015). Even more important, due to insertional mutagenesis of retroviral vectors, the clinical use of retroviral approaches is a critical safety concern with genotoxic effects revealed in clinical studies (Aiuti & Roncarolo 2009; Aiuti et al. 2009).

Within the group of retroviral vectors, lentiviral vectors however are less genotoxic and represent a safer option for clinical applications (Montini et al. 2009; Papayannakos & Daniel 2013). Unfortunately, even after stimulation with different cytokine combinations and using high lentiviral vector titers, only around 10% of NK cells can be transduced, which can be explained by NK cells anti-viral defense mechanisms (Sutlu et al. 2012). This transduction efficiency can be increased to about 40% using high lentiviral vector titers together with protamine sulfate and BX795, an inhibitor of the TBK1/IKKe complex (Sutlu et al. 2012). However, TBK1 is essential for mitosis and BX795 is generally known to cause cell cycle arrest resulting in non-proliferating cells (Pillai et al. 2015; Bai et al. 2015). Thus, the critical and undesired side effects make BX795 unsuitable for clinical NK cell transduction where stable transduction and proper NK cell functionality, including robust cell proliferation, are urgently required.

In WO2013/045639A1 a method for transduction of quiescent HSCs and resting T and B cells is disclosed using a viral vector pseudotyped with a modified baboon endogenous retrovirus (BaEV) envelope glycoprotein.

In conclusion, methods and/or viral vector particle systems for efficient and durable genetic modification of NK cells, which can be clinically applied for therapy, represent an urgent need that is not met by the current state-of-the-art.

SUMMARY OF THE INVENTION

Surprisingly, it was found that after activation primary human NK cells can be efficiently transduced by using retrovirus vector particles such as lentiviral vector particles pseudotyped with a modified baboon endogenous retrovirus (BaEV) envelope glycoprotein as disclosed herein, even without the need for inhibitors of NK cells anti-viral defense mechanisms whereas resting NK cells cannot be efficiently transduced by these vector particles. Transduction is detectable even at low retroviral vector particles titers such as lentiviral vector particle titers and can reach more than 90%, which is unseen with other viral vector particles reported so far. The use of low vector particle titers results in better practicability compared to methods of the prior art. For example, the lentiviral vector particle with modified Baboon envelope protein as disclosed herein gives much higher transduction efficiency (7-10 fold higher) than vector particles with VSV-G envelope protein. The transduction method disclosed herein does not trigger cell death or show other toxic effects on the transduced NK cells. Furthermore, the method does not affect NK cells mitosis, thus transduced NK cells are highly proliferative over long time, at the same level as untransduced counterparts. Taken together, the absence of undesired side effects and the clinically-compliant nature of the used pseudotyped retroviral vector particle such as lentiviral vector particle, makes the method disclosed herein unique for stable genetic modification of NK cells for therapeutic applications.

Unexpectedly, activation of human NK cells and use of modified baboon endogenous retrovirus (BaEV) envelope glycoprotein pseudotyped retroviral vector particles as disclosed herein result in high frequencies of transduced NK cells. Preferentially, NK cells are activated by stimulating agents, either in soluble form or surface-bound or by feeder cells, including parts of feeder cells, such as membrane particles. More preferentially, NK cells are activated by at least one growth factor such as a cytokine or combinations of growth factors such as cytokines, e.g. common-gamma chain cytokines including but not limited to IL-2, IL-7, IL-15, IL-21 or IL-1 family cytokines including but not limited to IL-1alpha, IL1beta, IL-18, IL-33, 11-36, IL37 and IL38. Even more surprisingly, the transduction efficiency can be further increased by combining different cytokines together with a IL-1 family cytokine, e.g. IL-2 and/or IL-15 together with a IL-1 family cytokine such as IL-18, IL-33, or IL-1beta. The addition of IL-1 family cytokine such as IL-18, IL-33 or IL-1beta to other well-known cytokines that activate NK cells lead to a short-term activation of NK cells allowing to transduce the NK cells efficiently earlier than the use of NK activation methods of the prior art. i.e. without the presence of a IL-1 family cytokine. It is a surprising finding that under the conditions disclosed herein the percentage of activated NK cells transduced with the modified baboon endogenous retrovirus (BaEV) envelope glycoprotein pseudotyped viral vector particles as disclosed herein is not only very high, but also remains stable for several weeks without reduction of transgene expression. The duration of transgene expression may be maintained over e.g. 2, 4, 6, 8 or more weeks. The biological material may also be transferred into the activated NK cell by a modified baboon endogenous retrovirus (BaEV) envelope glycoprotein pseudotyped virus-like particle as disclosed herein instead of the virus vector particle.

Even more surprisingly, the enrichment of CX3CR1 negative NK cells before activation and transduction of these NK cells from a sample comprising CX3CR1 negative and CX3CR1 positive NK cells results in superior proliferation and transduction with the modified baboon endogenous retrovirus (BaEV) envelope glycoprotein pseudotyped viral vector particles as disclosed herein. The enrichment of CX3CR1 negative NK cells may be achieved by separating CX3CR1 positive and CX3CR1 negative cells from a sample or population of NK cells comprising CX3CR1 negative and CX3CR1 positive cells.

The method for transduction of activated NK cells as disclosed herein may also be fully implemented as an automated process, preferentially in a closed system under GMP conditions.

BRIEF DESCRIPTION OF THE DRAWINGS

FIG. 8: Naive as well as activated NK cells were subjected to westernblot to check the expression of baboon envelope receptor ASCT2. Activated but not naive NK cells expressed the receptor for baboon envelope ASCT2.

FIG. 9 A: Cell proliferation and transduction assays showed that only proliferative but not the quiescent NK cells are transducible with baboon pseudotyped lentiviral vector.

FIG. 9 B: Proliferative and transducible subsets of NK cells are CD56$^{bright}$. In contrary, non-proliferative and non-transducible NK cells are CD56$^{dim}$.

FIG. 12 A: Different NK cell subsets were separated based on their CX3CR1 expression using MCAS sorting prior to transduction and culture. Without sorting, the expression of CX3CR1 among blood derived NK cells from donor was 86% and CX3CR1$^{neg}$ NK cells were 14%. After sorting, the mean frequency of CX3CR1$^{neg}$ NK cells was reduced to 2% by enrichment for CX3CR1, while depletion for the marker on the other hand led to enrichment of 91% CX3CR1$^{neg}$ NK cell population.

FIG. 12 B: Shortly after the cultivation of the differently sorted NK cell fractions, we observed significant differences in proliferation. Among the unsorted, CX3CR1 enriched (CX3CR1 positive) and CX3CR1 depleted (CX3CR1 negative) NK cell subsets, the percentage of NK cell proliferation was 28, 11 and 81, respectively.

FIG. 12 C: CX3CR1$^{neg}$ fraction of NK cells are highly transducible. 2 days after the transduction of sorted NK cells fraction, the transduction rate of unsorted, CX3CR1$^{enriched}$ and CX3CR1$^{depleted}$ NK cell subsets were 21%, 7%, and 69%, respectively.

DETAILED DESCRIPTION OF THE INVENTION

Figure 1:
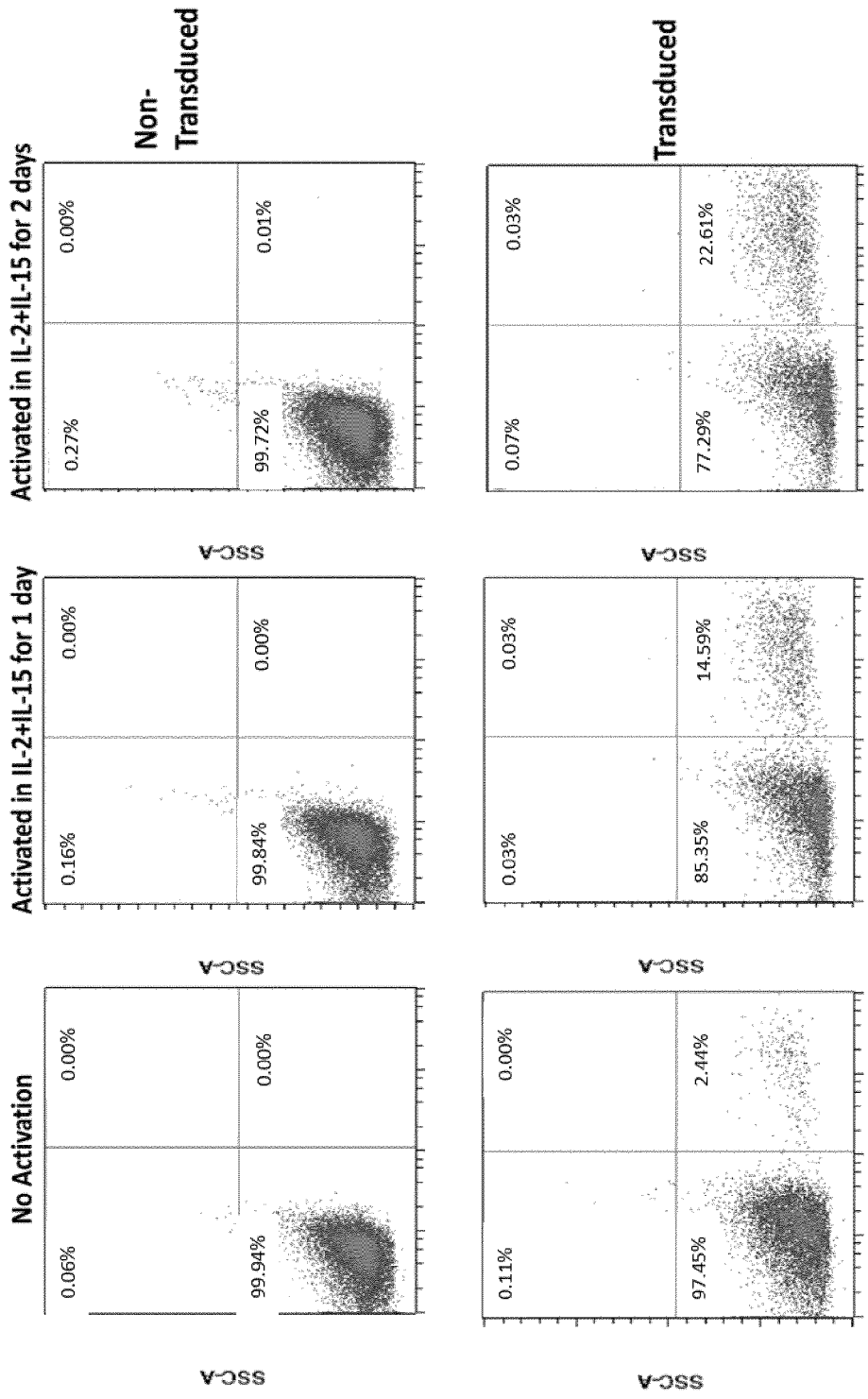
FIG. 1: BaEV pseudotyped vector allows high transduction of NK cells, as demonstrated by the expression of GFP, but the NK cells need to be activated FIG. 2 A: CD3$^+$ T cells and CD3$^-$/CD56$^+$ NK cells used in the experiments were isolated from PBMC resulting in highly purified cell populations FIG. 2 B: Transduction of T cells with a VSV-G pseudotyped lentiviral vector works, while it is extremely inefficient for NK cells even at high titers FIG. 2 C: Transduction with VSV-G pseudotyped lentiviral vector for the NK-92 cell line is similarly inefficient as for primary NK cells, but surprisingly NK-92 can be efficiently transduced with BaEV pseudotyped vector FIG. 2 D: T cells and activated primary NK cells both can be transduced very efficiently with baboon envelope pseudotyped lentiviral vector FIG. 3 A: Surprisingly, short activation of NK cells with IL-33 allows higher transduction rates of NK cells with BaEV pseudotyped vector than without IL-33

In one aspect the present invention provides an in-vitro method for transferring biological material into activated NK cells with a pseudotyped retroviral vector particle or a virus-like particle thereof, comprising the steps
 a) Activation of NK cells, and
 b) Addition of said pseudotyped retroviral vector particle or virus-like particle thereof to said activated NK cells, wherein said pseudotyped retroviral vector particle or virus-like particle thereof comprises a modified baboon endogenous retrovirus (BaEV) envelope glycoprotein that is able of binding to and fusing with a hematopoietic cell membrane, thereby transferring biological material into said activated NK cells.

Said method, wherein said NK cells are human NK cells.

Said method, wherein said NK cells to be activated are in a sample comprising NK cells, e.g. a whole blood sample or a peripheral blood mononuclear cell (PBMC) sample that e.g. may be obtained from buffy coat.

Said method, wherein prior to said activation of NK cells, the NK cells may be enriched for CX3CR1 negative NK cells from a population or sample comprising CX3CR1 positive and CX3CR1 negative NK cells.

Said enrichment of CX3CR1 negative NK cells or CX3CR1 negative NK cell subsets/subpopulations may be performed by depletion of the CX3CR1 negative cells in a separation process from a sample or population comprising CX3CR1 positive and CX3CR1 negative NK cells, wherein the depleted fraction is the target fraction that comprises the CX3CR1 negative cells, e.g. by separation methods such as cell separation methods, e.g. MACS® (Miltenyi Biotec GmbH) or fluorescence activated cell sorting such as flow cytometry using anti-CX3CR1 antibodies or fragments thereof.

A CX3CR1 negative NK cell subpopulation (or a CX3CR1 negative NK cell) is preferred to be transduced with the method as disclosed herein as it achieves extremely high transduction rates (see Example 9).

Said method, wherein said NK cells to be activated in step a) are CX3CR1 negative NK cells. Preferentially said CX3CR1 negative NK cells comprise less than 20%, 15%, 10%, 5%, or 1% CX3CR1 positive NK cells in a composition comprising NK cells that is used to be activated within the method as disclosed herein.

Pseudotyped retroviral vector particles or virus like particles thereof comprising modified baboon endogenous retrovirus (BaEV) envelope glycoproteins that are able of binding to and fusing with a hematopoietic cell membrane are well-known in the art and are disclosed for example in WO2013/045639A1.

Said pseudotyped retroviral vector particle or virus like particle thereof, wherein said modified baboon endogenous retrovirus (BaEV) envelope glycoprotein that is able of binding to and fusing with a hematopoietic cell membrane may be:
 a chimeric envelope glycoprotein which comprises or consists in a fusion of the transmembrane and extracellular domain of a baboon endogenous retrovirus (BaEV) envelope glycoprotein and the cytoplasmic tail domain of a murine leukemia virus (MLV) envelope glycoprotein; or
 a modified BaEV envelope glycoprotein wherein the cytoplasmic tail domain is devoid of the fusion inhibitory R peptide.

Said pseudotyped retroviral vector particle or virus like particle thereof may comprise at least: a chimeric envelope glycoprotein which comprises or consists in a fusion of the transmembrane and extracellular domain of a baboon endogenous retrovirus (BaEV) envelope glycoprotein and the cytoplasmic tail domain of a murine leukemia virus (MLV) envelope glycoprotein; or a modified BaEV envelope glycoprotein wherein the cytoplasmic tail domain is devoid of the fusion inhibitory R peptide.

Said method, wherein said activation of said NK cells may be achieved by the addition of at least one cytokine or feeder cells or membrane particles of feeder cells or with an NK cell activation reagent to said NK cells. Regularly, after 2 to 3 days the effect of NK cell activation leads to NK cell proliferation.

Said method, wherein said at least one cytokine is selected from the group consisting of common-gamma chain cytokines including but not limited to IL-2, IL-7, IL-15, IL-21 or IL-1 family cytokines including but not limited to IL-la (IL-1alpha), IL1b (IL-1beta), IL-18, IL-33, 11-36, IL37 and IL38.

Said at least one cytokine may be IL-2.

Said at least one cytokine may be IL-15.

Said cytokines may be IL-2 and IL15.

Said method, wherein a cytokine or a combination of cytokines that activate NK cells (such as IL-2 and/or Il-15) is combined with a IL-1 family cytokine, thereby leading to an earlier activation ("a short term activation") of said NK cells compared to the activation without the IL-1 family cytokine.

Said method, wherein said activation of NK cells achieved by the addition of a combination of cytokines comprising at least one cytokine that activates NK cells and a IL-1 family cytokine, thereby leading to a short-term activation of NK cells.

Said method, wherein said combination of cytokines are IL-2 and/or IL-15 and a IL-1 family cytokine. The use of one or more cytokines that activate NK cells (such as IL-2 and/or IL-15) together with a IL-1 family cytokine (such as IL-18 or IL-33) leads to a short-term activation that reduces e.g. the period between start of a culturing process for activation of NK cells and the start point that allow an efficient transduction of the activated NK cells with the retroviral vector particle as disclosed herein. Surprisingly, the combination of a IL-1 family cytokine and one or more cytokines that activate NK cells (such as IL-2 and/or IL-15) and the transduction with the retroviral vector particle as disclosed herein leads to higher transduction rates compared to transduction of the retroviral vector particle into NK cells that have been activated in a longer process, i.e. that did not benefit from the short-term activation process induced by the presence of a IL-1 family cytokine such as IL-18, IL-33 or IL-1beta.

Said IL-1 family cytokine may be selected from the group consisting of IL-1alpha, IL-1beta, IL-1Ra, IL-18, IL-36Ra, IL-36alpha, IL-37, IL-36beta, IL-36gamma, IL-38 and IL-33. Preferentially, said IL-1 family cytokine may be IL-18, IL-33 or IL-1beta.

Said method, wherein said IL-1 family cytokine is IL-18, thereby leading to short term activation within 1 hour, 2 hours, 4 hours, 8 hours, 12 hours, 18 hours, 24 hours (1 day), 28 hours, 36 hours, 42 hours or 48 hours (2 days).

Said method, wherein said IL-1 family cytokine is IL-33, thereby leading to short term activation within 1 hour, 2 hours, 4 hours, 8 hours, 12 hours, 18 hours, 24 hours (1 day), 28 hours, 36 hours, 42 hours or 48 hours (2 days).

The addition of a IL-1 family cytokine such as IL-18, IL-33 or IL-1beta e.g. at the beginning of a cell culture system together with other cytokines known to activate NK cells to a medium comprising NK cells leads to an activation of said NK cells as early as 1 hour, 2 hours, 4 hours, 8 hours, 12 hours, 18 hours, 24 hours (1 day), 28 hours, 36 hours, 42 hours or 48 hours (2 days) after the addition of said IL-1 family cytokine. Therefore, the addition of a IL-1 family cytokine to the NK cells, preferentially in a cell culture medium, leads within 1 hour, 2 hours, 4 hours, 8 hours, 12 hours, 18 hours, 24 hours (1 day), 28 hours, 36 hours, 42 hours or 48 hours (2 days). to a short term activation of the NK cells.

The cytokines described above may be given to a cell culture medium comprising said NK cells in concentrations well-known to the person skilled in the art and that are commonly used. Said method, wherein said activation of said NK cells may be achieved by the addition of one IL-1 family cytokine without other cytokines or feeder cells or membrane particles of feeder cells or with an NK cell activation reagent to said NK cells.

Said method, wherein said activation of said NK cells may be achieved by the addition of one IL-1 cytokine together with feeder cells or membrane particles of feeder cells or with an NK cell activation reagent to said NK cells.

Said method, wherein the transduction efficiency of the NK cells by said pseudotyped retroviral vector particle is at least 50%, at least 60%, at least 70%, at least 80% or at least 90%. Said method, wherein said biological material is one or more nucleic acids if the said NK cell is transduced with said retroviral vector particle.

Said method, wherein said retroviral vector particle or virus-like particle thereof is a lentiviral vector particle or virus-like particle thereof.

Said method, wherein said method is performed in an automated process in a closed system. In another aspect the present invention provides a pseudotyped retroviral vector particle or virus-like particle thereof for the use in treatment of a human suffering from a disorder by transferring in-vivo biological material into an activated NK cell, wherein said pseudotyped retroviral vector particle or virus-like particle thereof comprises a modified baboon endogenous retrovirus (BaEV) envelope glycoprotein as disclosed herein that is able of binding to and fusing with a hematopoietic cell membrane, thereby transferring biological material into said activated NK cells.

The disorder may be a disorder that may be treated or treatable with said NK cells.

In a further aspect the present invention provides a combination of compositions for use in treatment of a human suffering from a disorder by transferring in-vivo biological material into activated NK cells, comprising
 a) A first composition comprising at least one cytokine that activates NK cells, and
 b) A composition comprising a pseudotyped retroviral vector particle or virus-like particle thereof, wherein said pseudotyped retroviral vector particle or virus-like particle thereof comprises a modified baboon endogenous retrovirus (BaEV) envelope glycoprotein as disclosed herein that is able of binding to and fusing with a hematopoietic cell membrane The disorder may be a disorder that may be treated or treatable with said NK cells.

Said combination of compositions, wherein said first composition comprises a combination of cytokines comprising at least one cytokine that activates NK cells and a IL-1 family cytokine. Said combination of compositions, wherein said combination of cytokines comprises IL-2 and/or IL-15 and a IL-1 family cytokine.

Said combination of compositions, wherein said IL-1 family cytokine is IL-18, IL-33 or IL-1beta.

Said combination of compositions for preparing engineered NK cells.

Said combination of compositions, wherein said biological material is a nucleic acid encoding for a chimeric antigen receptor.

In another aspect the present invention provides the use of a pseudotyped retroviral vector particle or virus-like particle thereof for transferring biological material into an activated NK cell, wherein said pseudotyped retroviral vector particle or virus-like particle thereof comprises a modified baboon endogenous retrovirus (BaEV) envelope glycoprotein as disclosed herein that is able of binding to and fusing with a hematopoietic cell membrane.

Said use of a pseudotyped retroviral vector particle or virus-like particle thereof for preparing engineered NK cells.

Said use of a pseudotyped retroviral vector particle or virus-like particle thereof, wherein said biological material is a nucleic acid encoding for a chimeric antigen receptor.

In a further aspect the present invention provides a transduced and/or engineered NK cell obtainable by the method as disclosed herein.

Said engineered NK cell, wherein said NK cell is engineered to express a chimeric antigen receptor.

In one aspect the present invention provides a pharmaceutical composition of engineered NK cells obtained by the methods as disclosed herein.

Said pharmaceutical composition, wherein said engineered NK cells express a chimeric antigen receptor.

In another aspect the present invention provides a combination of cytokines for short term-activation of NK cells comprising at least one cytokine that activates NK cells and a IL-1 family cytokine.

Said combination of cytokines may be IL2 and/or IL-15 and a IL-1 family cytokine. Said IL-1 family cytokine may be IL-18, IL-33 or IL-1beta.

All definitions, characteristics and embodiments defined herein with regard to an aspect of the invention, e.g. the first aspect of the invention, also apply mutatis mutandis in the context of the other aspects of the invention as disclosed herein.

Definitions

Unless defined otherwise, technical and scientific terms used herein have the same meaning as commonly understood by one of ordinary skill in the art to which this invention belongs.

Retroviridae is virus family with a single-stranded, diploid, positive-sense RNA genome that is reverse-transcribed into a DNA intermediate that is then incorporated into the host cell genome. Retroviridae-derived viruses are enveloped particles with a diameter of 80-120 nm. (Retro-/lenti-/gammaretro-) viral vectors are replication-deficient viral particles that are derived from the corresponding virus family. They contain Gag and Pol proteins, a single-stranded RNA genome and are usually pseudotyped with heterologous envelope proteins derived from other viruses, e.g. with a baboon endogenous retrovirus (BaEV) envelope glycoprotein as disclosed herein. The RNA genome of said viral vectors do not contain any viral gene to produce viral progeny, but psi elements and LTRs that are required for efficient packing and reverse transcription in DNA. The DNA intermediate may contain a gene of interest under the control of a suitable promoter, for example, the CMV promoter and the gene of interest is expressed upon integration of said DNA into the genome of the host cell. The process of entering the host cell, delivering the RNA genome, integration and expression of the gene of interest is called transduction. The minimal requirements of a gammaretrovirus or lentivirus based viral vector has been well-described in the art.

In addition, integrase-deficient retroviral vectors (ID-RVs) have been developed that cannot integrate the retroviral vector genome in the host cell genome. ID-RVs are derived from conventional retroviral vectors but contain no or a mutated form of the retroviral integrase. Upon entry into the host cell, the retroviral vector genome is reverse-transcribed in the cytoplasm, delivered into the nucleus, but not stably integrated into the host cell genome. ID-RVs are a useful tools to express the gene of interest transiently. The definition of retroviral vectors and transduction also extents the integration-deficient retroviral vectors and its application.

Lentivirus is a genus of Retroviridae that cause chronic and deadly diseases characterized by long incubation periods, in the human and other mammalian species. The best known lentivirus is the Human Immunodeficiency Virus HIV which can efficiently infect nondividing cells, so lentiviral derived retroviral vectors are one of the most efficient methods of gene delivery. Gammaretroviridae is a genus of the Retroviridae family. Representative species are the murine leukemia virus and the feline leukemia virus.

Virus-like particles (VLPs) resemble viral particles, but are not infecting or transducing because they contain no viral genetic material encoding for the proteins of the virus-like particle. In particular, VLPs in the context of retroviral vectors do not contain psi positive nucleic acid molecules. Some virus-like particles may contain nucleic acid distinct from their genome. The expression of viral structural proteins, such as envelope or capsid, can result in the assembly of virus like particles (VLPs). Like for retroviral vectors VLPs can also be pseudotyped using the same envelope constructs as for retroviral vectors. VLPs may be used to deliver proteins but also nucleic acids to the cytoplasm of target cells. In particular, VLPs are useful as vaccines. The term "VLP uptake" as used herein refers to the binding of a VLP to the target cell membrane, thereby releasing nucleic acid molecules, proteins or peptides into the target cell. The term "activation" as used herein refers to inducing physiological changes with a cell that increase target cell function, proliferation and/or differentiation.

The term "pseudotyping" or "pseudotyped" as used herein refers to a vector particle bearing envelope glycoproteins derived from other viruses having envelopes. The host range of the lentiviral vectors or vector particles of the present invention can thus be expanded or altered depending on the type of cell surface receptor used by the glycoprotein.

To generate retroviral vectors the gag, pol and env proteins needed to assemble the vector particle are provided in trans by means of a packaging cell line, for example, HEK-293T. This is usually accomplished by transfection of the packaging cell line with one or more plasmids containing the gag, pol and env genes. For the generation of pseudotyped vectors, the env gene, originally derived from the same retrovirus as the gag and pol genes and as the RNA molecule or expression vector, is exchanged for the envelope protein(s) of a different enveloped virus.

The Baboon endogenous retrovirus or BaEV is a type C retrovirus present in multiple proviral copies in the DNA of baboons. In WO2013045639A1 the wild-type BaEV envelope glycoprotein (non-modified BaEV envelope glycoprotein) and BaEV envelope glycoproteins having defined mutations (modifications) that were incorporated at a higher level on the lentiviral surface than the wild-type BaEV glycoprotein are described in detail.

The term "BaEV envelope glycoprotein" as used herein refers to the wild-type form of the BaEV envelope glycoprotein or to a mutant of said wild-type BaEV envelope glycoprotein which is at least 80%, at least 85%, at least 90%, at least 95%, or at least 99% identical to said wild-type BaEV envelope glycoprotein, provided that said mutant glycoprotein retains the capacity of the wild-type glycoprotein of binding to and fusing with hematopoietic cells membrane.

Preferably, the wild-type BaEV envelope glycoprotein consists of the sequence SEQ ID NO: 1. As known from the skilled person, the BaEV envelope glycoprotein is constituted by a cytoplasmic tail domain, a transmembrane domain and an extracellular domain. The regions corresponding to the cytoplasmic tail domain, the transmembrane domain and extracellular domain in the envelope glycoprotein sequence can be easily determined by the skilled person. Typically, the cytoplasmic tail domain is located between amino acids 530 to 564 of the wild-type BaEV envelope glycoprotein. Typically, the transmembrane domain is located between amino acids 507 to 529 of the wild-type BaEV envelope glycoprotein. Typically, the extracellular domain is located between amino acids 1 to 506 of the wild-type BaEV envelope glycoprotein.

In a particular embodiment of the invention, the cytoplasmic tail domain of the BaEV envelope glycoprotein is devoid of the fusion inhibitory R peptide.

In the context of the invention, the expression "fusion inhibitory R peptide" refers to the C-terminal portion of the cytoplasmic tail domain of the envelope glycoprotein which harbours a tyrosine endocytosis signal—YXXL—(SEQ ID NO:2) and which is cleaved by viral protease during virion maturation, thus enhancing membrane fusion of the envelope glycoprotein. The fusion inhibitory R peptide of the BaEV envelope glycoprotein is typically located between amino acids 547 and 564 of the wild-type BaEV envelope glycoprotein.

Therefore, in a particularly preferred embodiment, the modified BaEV envelope glycoprotein wherein the cytoplasmic tail domain is devoid of the fusion inhibitory R peptide comprises or consists in the amino acid sequence SEQ ID NO: 3.

In another particular embodiment, the cytoplasmic tail domain of the BaEV envelope glycoprotein is replaced by the cytoplasmic tail domain of a murine leukemia virus (MLV) envelope glycoprotein.

The Murine Leukemia Virus envelope glycoprotein is preferably that of strain 4070A.

In the context of the invention, the term "MLV envelope glycoprotein" refers to the wild-type form of the MLV envelope glycoprotein or to a mutant of said wild-type MLV envelope glycoprotein which is at least 80%, at least 85%, at least 90%, at least 95%, at least 99% identical to said wild-type MLV envelope glycoprotein, provided that said mutant glycoprotein retains the capacity of the wild-type envelope glycoprotein of interacting with viral core proteins, in particular with lentiviral core proteins.

The region corresponding to the cytoplasmic tail domain in the envelope glycoprotein sequence can be easily determined by the skilled person. Typically, the cytoplasmic tail domain of the MLV envelope glycoprotein is located between amino acids 622 and 654 of the wild-type MLV envelope glycoprotein.

Therefore, in a particularly preferred embodiment, the chimeric envelope glycoprotein which comprises or consists in a fusion of the transmembrane and extracellular domain of a BaEV envelope glycoprotein and the cytoplasmic tail domain of a MLV envelope glycoprotein comprises or consists in the amino acid sequence SEQ ID NO: 4.

As intended herein the expression "biological material" relates to one or more compounds liable to alter the structure and/or the function of a cell. Within the context of the present invention, it is preferred that the biological material is one or more nucleic acids, which in the case of lentiviral vector particles may be comprised within the genome of the vector particle.

As intended herein "transferring" relates to the capacity of the vector particle or vector-like particle to initially deliver the biological material to the membrane or the cytoplasm of the target cell, upon being bound to the target cell. Herein, usually the target cell is an NK cell.

The term "natural killer cells (NK cells)" as used herein are regularly human NK cells and are defined as large granular lymphocytes (LGL) and constitute the third kind of cells differentiated from the common lymphoid progenitor-generating B and T lymphocytes. NK cells are known to differentiate and mature in the bone marrow, lymph nodes, spleen, tonsils, and thymus, where they then enter into the circulation. NK cells differ from natural killer T cells (NKTs) phenotypically, by origin and by respective effector functions; often, NKT cell activity promotes NK cell activity by secreting IFNγ. In contrast to NKT cells, NK cells do not express T-cell antigen receptors (TCR) or pan T marker CD3 or surface immunoglobulins (Ig) B cell receptors, but they usually express the surface markers CD16 (FcγRIII) and CD56 in humans, NK1.1 or NK1.2 in C57BL/6 mice. Up to 80% of human NK cells also express CD8. Continuously growing NK cell lines can be established from cancer patients and common NK cell lines are for instance NK-92, NKL and YTS.

The terms "Titer" or "transduction efficiency" is used as a means to characterize and compare vector particles with regard to their ability to transduce their target cells. Thus, vector particles having an "increased titer" or an "increased transduction efficiency" are able to transduce a higher number of cells at a given vector particle volume than other vector particles with the same volume.

The term "activated NK cell" as used herein refers to a change of the cells compared to naive, freshly isolated, non-activated NK cells by a stimulating condition, manifesting itself in a changed gene expression profile or changed cell signaling, leading to NK cells with different cellular properties compared to non-activated NK cells. "Activated NK cells" may for example increase the expression of certain surface receptors, such as NKp44, NKG2D, DNAM-1 or TRAIL, or change the expression of cytokine receptors, for example up-regulate CD25. Activated NK cells may change their cell cycle phase from quiescent cells in G0, to G1, S, or G2, and may start to proliferate or proliferate faster.

The term "CX3CR1 negative NK cells" or "CX3CR1$^{neg}$ NK cells" or "CX3CR1$^-$ NK cells" or "CX3CR1 depleted NK cells" or "CX3CR1$^{depleted}$ NK cells" refer to a population of NK cells that do not express the marker CX3CR1 on their cell surface.

CX3C chemokine receptor 1 (CX3CR1) also known as the fractalkine receptor or G-protein coupled receptor 13 (GPR13) is a protein that in humans is encoded by the CX3CR1 gene. As the name suggests, this receptor binds the chemokine CX3CL1 (also called neurotactin or fractalkine).

The term "short-term activation" as used herein refers to the possibility of faster activation of NK cells by the addition of a Il-1 family cytokine e.g. to the cell culture media comprising NK cells to be activated compared to the standard NK cell activation using e.g. different cytokines known to activate NK cells but no IL-1 family cytokine. NK cell activation occurs in the presence of a IL-1 family already after 1 hour, 2 hours, 4 hours, 8 hours, 12 hours, 18 hours, 24 hours (1 day), 28 hours, 36 hours, 42 hours or 48 hours (2 days).

The term "NK cell activation reagent" refers to a molecule such as a particle, bead or nanomatrix that has coupled thereto one or more stimulatory agents that provide activation signals to NK cells such as stimulating antibodies against CD2 and CD335. An example for such an NK cell activation reagent is Miltenyi Biotec's NK Cell Activation/Expansion Kit (Miltenyi Biotec GmbH, Bergisch Gladbach, Germany, Order no. 130-094-483) or the nanomatrix described in EP2824112B1.

The Interleukin-1 family (IL-1 family) is a group of 11 cytokines, which plays a central role in the regulation of immune and inflammatory responses to infections or sterile insults.

Said IL-1 family cytokine are IL-1alpha, IL-1beta, IL-1Ra, IL-18, IL-36Ra, IL-36alpha, IL-37, IL-36beta, IL-36gamma, IL-38 and IL-33. As disclosed herein the addition of a IL-1 family cytokine to a standard (prior art) NK cell activation process using e.g. other cytokines speeds up NK cell activation leading to a short-term activation of NK cells.

The IL-1 family cytokine can also be a variant thereof which have some amino acids deleted, added or replaced while still retaining the function of the cytokine. Therefore, included in this definition are variants of the amino acid sequence of the wild-type cytokine having a sequence identity of at least 70%, or at least 75%, 80%, 85%, 90%, 95%, 97%, 98% or 99% at the amino acid sequence level. In the context of the present invention, "sequence identity" may be determined using pairwise alignments using alignments programs for amino acid sequences well known to the art.

The IL-1 family cytokine may also be a functional fragment of the full-length cytokine having a sequence identity of at least 70%, or at least 75%, or at least 80%, or at least 85%, or at least 90%, or at least 95%, or at least 97%, or at least 98%, or at least 99% at the amino acid sequence level to the corresponding part of said full-length cytokine ("Il-1 family cytokine or a functional fragment thereof").

In general, all amino acid variations (i.e. substitutions, additions or eliminations of amino acids of the Il-1 family cytokine) are included under this definition, which do not lead to the loss of the characteristics of the Il-1 family cytokine as disclosed herein.

The term "expression" as used herein is defined as the transcription and/or translation of a particular nucleotide sequence driven by its promoter in a cell.

The term "feeder cells" refers to cells that are added to a culture of target cells (i.e. here Natural Killer cells) to support their survival and/or growth. Feeder cells provide an intact and functional extracellular matrix and matrix-associated factors and secrete known and unknown cytokines into the conditioned medium. Feeder cells are usually growth arrested to prevent their proliferation in the culture, but their survival is maintained. Growth arrest can be achieved by irradiation with an effective dose or treatment with an effective dose of chemicals such as Mytomycin C. There are several kind of feeders cells including irradiated Peripheral Blood Mononuclear cells (hereinafter also abbreviated as "PBMC"), PBMCs depleted of NK cells, cancer cell lines, genetically engineered cancer cell lines and lymphocytes immortalized by natural infection with Epstein-Barr Virus (hereinafter also abbreviated as "EBV").

As used herein the term "culturing" includes providing the chemical and physical conditions (e.g., temperature, gas) which are required for NK cell maintenance, and growth factors. Often culturing the NK cells includes providing the NK cells with conditions for expansion (proliferation). Examples of chemical conditions which may support NK cell expansion include but are not limited to buffers, serum, nutrients, vitamins, antibiotics, cytokines and other growth factors which are regularly provided in (or may be given manually to) the cell culture medium suited for NK cell expansion. In one embodiment, the NK cell culture medium includes NK MACS Research Medium (Miltenyi Biotec GmbH) supplemented with 5% human serum type AB (Life Technologies), 500 U/mL of IL-2 (Miltenyi) and 10 ng/mL IL-15 (Miltenyi). Other media suitable for use to expand NK cells are well known in the art.

The term "cell culture medium" as used herein includes liquids providing the chemical conditions which are required for NK cell maintenance. Examples of chemical conditions which may support NK cell expansion include but are not limited to solutions, buffers, serum, serum components, nutrients, vitamins, cytokines and other growth factors which are regularly provided in (or may be given manually to) the cell culture medium. Media suitable for use to cultivate NK cells as known in the art include NK MACS (Miltenyi), TexMACS (Miltenyi), CellGro SCGM (CellGenix), X-Vivo 10, X-Vivo 15, BINKIT NK Cell Initial Medium (Cosmo Bio USA), AIM-V (Invitrogen), DMEM/F12, NK Cell Culture Medium (upcyte technologies). The terms "IL-2" and "IL-15" as used herein refer to cytokines Interleukin-2 and Interleukin-15 and derivatives thereof e.g. IL-2 superkine, IL-2 diphteria toxin fusion protein or IL-15Ra sushi.

The term IL-2 and/or IL-15 generally refers to members of the 4α-helix bundle family of cytokines binding to the heterotrimeric receptors for IL2 and IL15 sharing the common gamma chain and IL2/IL15Rβ (also known as IL2Rβ, CD122).

The term "adding (repeatedly) an effective concentration of IL-2 and/or IL-15" as used herein refers to concentrations of IL-2 in said cell culture medium between 1 U/mL and 5000 U/mL, preferentially between 10 U/mL and 1000 U/mL, more preferentially between 50 and 500 U/mL, and/or refers to concentrations of IL-15 in said cell culture medium between 0.1 and 1000 ng/mL, preferentially between 1 and 200 ng/mL, more preferentially between 10 and 100 ng/mL. Normally, the concentration of IL-2 and/or IL-15 decreases with time during the culturing process, therefore IL-2 and/or IL-15 may be added repeatedly to the cell culture medium to maintain the levels of the cytokine(s) at the effective concentration(s). Regularly, IL-2 and/or IL-15 may be added again to the cell culture by a cell culture medium change. In this context "repeatedly" means at least one repeat within the whole culturing process. It is not necessary to add IL-2 and/or IL-15 at the beginning of the culturing process but at least at the first medium change, i.e. after 7 days. But nonetheless, the adding of IL2 and/or IL-15 at the beginning of the culturing process is advantageous.

As used herein, the term "expansion" or "proliferation" refers to cell growth and multiplication of cell numbers. Expansion or proliferation, as used herein relate to increased numbers of NK cells occurring during the cultivation process.

The terms "culturing process" or "cultivation" as used herein refer to the culturing and expansion of NK cells, wherein the starting day (starting point) of the culturing process, i.e. the expansion of NK cells, is defined as day 0. The culturing process may last as long as desired by the operator and can be performed as long as the cell culture medium has conditions which allow the cells to survive and/or grow and/or proliferate.

The term "beginning of the culturing process" as used herein refers to the start of the expanding process by adding growth factors such as IL-2 and/or IL-15 to the cell culture medium, i.e. the cells are initiated to start their proliferation process. The addition of a IL-1 family cytokine such as IL-18 or IL-33 accelerates the activation process of the NK cells and prepares for efficient transduction, therefore the IL-1 family cytokine should be given to the medium together with other, well-known cytokines that activate NK cells. Preferentially, the effective concentration of a IL-1 family cytokine is added once to the cell culture medium only. Alternatively, the effective concentration of a IL-1 family cytokine is added repeatedly, e.g. twice or more frequently, to said cell culture medium.

The term "adding (repeatedly) an effective concentration of a IL-1 family cytokine" as used herein refers to concentrations of said IL-1 family cytokine in said cell culture medium between 1 U/mL and 5000 U/mL, preferentially between 10 U/mL and 1000 U/mL, more preferentially between 50 and 500 U/mL. The term "membrane particles of feeder cells" as used herein refers to membrane preparations of the feeder cells that contain the NK cell stimulating surface molecules of the feeder cells. Membrane particles of the feeder cells may be utilized to avoid possible disadvantages of live feeder cells. Membrane particles of feeder cells can be produced by lysis and disruption of the cells using nitrogen cavitation followed by isolation and purification of the cell membrane fraction by density gradient centrifugation, exemplary described by Oyer et al. (Oyer 2015). Normally, in the method disclosed herein the feeder cells can be replaced by membrane particles of said feeder cells. Preferentially, the membrane particles should be used in such amounts that is comparable to these amounts that can be obtained by the used live feeder cells. Preferentially the concentration of used membrane particles may be between 100 and 400 µg/mL, more preferentially between 150 and 250 µg/mL. The addition of membrane particles may be performed as frequently as the addition of live feeder cells.

The terms "engineered cell" and "genetically modified cell" (herein especially NK cells) as used herein can be used interchangeably. The terms mean containing and/or expressing a foreign gene or nucleic acid sequence which in turn modifies the genotype or phenotype of the cell or its progeny. Especially, the terms refer to the fact that cells can be manipulated by recombinant methods well known in the art to express stably or transiently peptides or proteins which are not expressed in these cells in the natural state. The term "closed system" as used herein refers to any closed system which reduces the risk of cell culture contamination while performing culturing processes such as the introduction of new material and performing cell culturing steps such as proliferation, differentiation, activation, and/or separation of cells. Such a system allows to operate under GMP or GMP-like conditions ("sterile") resulting in cell compositions which are clinically applicable. Herein exemplarily the CliniMACS Prodigy® (Miltenyi Biotec GmbH, Germany) is used as a closed system. This system is disclosed in WO2009/072003. But it is not intended to limit the use of the method of the present invention to the CliniMACS® Prodigy. The terms "automated method" or "automated process" as used herein refer to any process being automated through the use of devices and/or computers and computer software which otherwise would or could be performed manually by an operator. Methods (processes) that have been automated require less human intervention and less human time to deliver. In some instances the method of the present invention is automated if at least one step of the present method is performed without any human support or intervention. Preferentially the method of the present invention is automated if all steps of the method as disclosed herein are performed without human support or intervention. Preferentially the automated process is implemented on a closed system such as CliniMACS® Prodigy. CARs comprise a single chain fragment variable (scFv) of an antibody specific for a certain target antigen coupled via hinge and transmembrane regions to cytoplasmic domains of cell signaling molecules. The most common lymphocyte activation moieties include a cell co-stimulatory (e.g. CD28, CD137, OX40, ICOS, and CD27) domain in tandem with a cell triggering (e.g. CD3ζ) moiety. The CAR-mediated adoptive immunotherapy allows CAR-grafted cells to directly recognize the desired antigen on target cells in a non-HLA-restricted manner.

Embodiments

In one embodiment of the invention a transgenic nucleic acid, e.g. a nucleic acid encoding for a chimeric antigen receptor is transferred into an activated NK cell with a retroviral vector particle, e.g. a lentiviral vector particle, that is pseudotyped with a modified baboon endogenous retrovirus (BaEV) envelope glycoprotein that is able of binding to and fusing with a hematopoietic cell membrane.

Said pseudotyped retroviral vector particle, e.g. lentiviral vector particle may comprise a chimeric envelope glycoprotein which comprises or consists in a fusion of the transmembrane and extracellular domain of a baboon endogenous retrovirus (BaEV) envelope glycoprotein and the cytoplasmic tail domain of a murine leukemia virus (MLV) envelope glycoprotein or a modified BaEV envelope glycoprotein wherein the cytoplasmic tail domain is devoid of the fusion inhibitory R peptide.

NK cells in a cell culture medium comprising NK cells are activated, e.g. by the addition of IL-2 and/or IL-15 to the medium. After 2 to 5 days the effect of NK cell activation leads to NK cell proliferation. Then said pseudotyped retroviral vector particle, e.g. lentiviral vector particle may be added to the medium, i.e. to the activated NK cells. The activated NK cells are transduced by said vector particle, expand in the medium and express the transgene, e.g. the chimeric antigen receptor.

These engineered NK cells may be used to treat a subject in need thereof.

In another embodiment of the invention a transgenic nucleic acid, e.g. a nucleic acid encoding for a chimeric antigen receptor is transferred into an activated NK cell with a retroviral vector particle, e.g. a lentiviral vector particle, that is pseudotyped with a modified baboon endogenous retrovirus (BaEV) envelope glycoprotein that is able of binding to and fusing with a hematopoietic cell membrane.

Said pseudotyped retroviral vector particle, e.g. lentiviral vector particle may comprise a chimeric envelope glycoprotein which comprises or consists in a fusion of the transmembrane and extracellular domain of a baboon endogenous retrovirus (BaEV) envelope glycoprotein and the cytoplasmic tail domain of a murine leukemia virus (MLV) envelope glycoprotein or a modified BaEV envelope glycoprotein wherein the cytoplasmic tail domain is devoid of the fusion inhibitory R peptide.

NK cells in a cell culture medium comprising NK cells are activated, by the addition of IL-2 and/or IL-15 and a IL-1 family cytokine, e.g. IL-18 or IL-33 to the medium. After 1 hour, 2 hours, 4 hours, 8 hours, 12 hours, 18 hours, 24 hours (1 day), 28 hours, 36 hours, 42 hours or 48 hours (2 days) the NK cells are activated. Then said pseudotyped retroviral vector particle, e.g. lentiviral vector particle is added to the medium, i.e. to the activated NK cells. The activated NK cells are transduced by said vector particle, expand in the medium and express the transgene, e.g. the chimeric antigen receptor.

These engineered NK cells may be used to treat a subject in need thereof.

In one embodiment of the invention said NK cells in a cell culture medium comprising a population of NK cells may be NK cells which are purified by CD3 depletion and CD56 enrichment using a clinical scale cell separator (CliniMACS plus, Miltenyi Biotec, Germany). These purified NK cells may be transduced with the retroviral vector particle or the virus-like particle thereof as disclosed herein.

In one embodiment of the invention said NK cells in a cell culture medium comprising a population of NK cells may be purified by CD3 depletion and CD56 enrichment including all magnetic labeling steps in a completely closed system (CliniMACS Prodigy®, Miltenyi Biotec, Germany).

These purified NK cells may be transduced with the retroviral vector particle or the virus-like particle thereof as disclosed herein.

In one embodiment of the invention said NK cells in a cell culture medium comprising a population of NK cells may be NK cells which are purified from a human blood sample such as PBMC by negative magnetic cell separation. The NK cells are separated by use of magnetic beads coupled to a cocktail of antibodies or fragment thereof binding to non-NK cells. The negative fraction comprising an enriched population of NK cells is then added to a cell culture medium suitable for activation of NK cells and subsequent transduction, i.e. the medium comprises Il-2 and/or IL-15 and/or IL-18.

These purified NK cells may be transduced with the retroviral vector particle or the virus-like particle thereof as disclosed herein.

In one embodiment of the invention said NK cells in a cell culture medium comprising a population of NK cells may be NK cells which are purified from whole human blood by negative magnetic cell separation and erythrocyte sedimentation as disclosed e.g. in WO2013076070A1 (MACSxpress® NK cell isolation kit, Miltenyi Biotec).

These purified NK cells may be transduced with the retroviral vector particle or the virus-like particle thereof as disclosed herein.

In one embodiment of the invention said NK cells in a cell culture medium comprising a population of NK cells may be NK cells which are purified subpopulations of NK cells. These purified NK cells may be transduced with the retroviral vector particle or the virus-like particle thereof as disclosed herein.

In one embodiment of the invention said NK cells in a cell culture medium comprising a population of NK cells may be NK cells which are purified CX3CR1 negative NK cell subpopulations. These purified NK cells may be transduced with the retroviral vector particle or the virus-like particle thereof as disclosed herein.

In one embodiment of the invention said NK cells in a cell culture medium comprising a population of NK cells may be NK cells which are purified KLRG1 or CD57 negative NK cell subpopulations. These purified NK cells may be transduced with the retroviral vector particle or the virus-like particle thereof as disclosed herein.

In one embodiment of the invention said NK cells in a cell culture medium comprising a population of NK cells may be NK cells which are purified NKG2C positive NK cell subpopulations. These purified NK cells may be transduced with the retroviral vector particle or the virus-like particle thereof as disclosed herein.

In one embodiment of the invention said NK cells in a cell culture medium comprising a population of NK cells may be NK cells which are purified memory like NK cell subpopulations. These purified NK cells may be transduced with the retroviral vector particle or the virus-like particle thereof as disclosed herein.

In one embodiment of the invention said NK cells in a cell culture medium comprising a population of NK cells may be NK cells which are cytokine induced memory like NK cells. These NK cells may be transduced with the retroviral vector particle or the virus-like particle thereof as disclosed herein.

In one embodiment of the invention said NK cells in a cell culture medium comprising a population of NK cells may be NK cells which are purified NK cell subpopulations positive for single KIR molecules or positive for specific KIR molecules. These purified NK cells may be transduced with the retroviral vector particle or the virus-like particle thereof as disclosed herein. In one embodiment of the invention said NK cells in a cell culture medium comprising a population of NK cells may be NK cells which are purified NK cell subpopulations that are specific for virus peptides. These purified NK cells may be transduced with the retroviral vector particle or the virus-like particle thereof as disclosed herein.

In one embodiment of the invention said NK cells in a cell culture medium comprising a population of NK cells may be NK cells which are enriched for a cytokine and chemokine secreting subpopulation. These enriched NK cells may be transduced with the retroviral vector particle or the virus-like particle thereof as disclosed herein.

In one embodiment of the invention said NK cells in a cell culture medium comprising a population of NK cells may be NK cells which are isolated subpopulations using a fluorescence activated cell sorter. These isolated NK cells may be transduced with the retroviral vector particle or the virus-like particle thereof as disclosed herein.

In one embodiment of the invention said NK cells in a cell culture medium comprising a population of NK cells may be NK cells which are isolated subpopulations using a microchip based cell sorter such as MACSQuant Tyto® (Miltenyi Biotec GmbH). These isolated NK cells may be transduced with the retroviral vector particle or the virus-like particle thereof as disclosed herein.

In one embodiment of the invention said NK cells in a cell culture medium comprising a population of NK cells that may be transduced with the retroviral vector particle or the virus-like particle thereof as disclosed herein to express a chimeric antigen receptor (CAR).

In one embodiment of the invention said NK cells in a cell culture medium comprising a population of NK cells that may be transduced with the retroviral vector particle or the virus-like particle thereof as disclosed herein to express a chimeric antigen receptor (CAR) that binds to a tagged protein, such as a biotinylated antibody.

In one embodiment of the invention said NK cells in a cell culture medium comprising a population of NK cells may be NK cells that may be transduced with the retroviral vector particle or the virus-like particle thereof as disclosed herein to express a T cell receptor (TCR).

In one embodiment of the invention said NK cells in a cell culture medium comprising a population of NK cells may be NK cells that may be transduced with the retroviral vector particle or the virus-like particle thereof as disclosed herein to express one or multiple chemokine receptors.

In one embodiment of the invention said NK cells in a cell culture medium comprising a population of NK cells may be NK cells that may be transduced with the retroviral vector particle or the virus-like particle thereof as disclosed herein to express a higher or lower affinity version of NK cell receptors than naturally occurring. Said NK cell receptors may be selected from the group of CD16, CD314/NKG2D, CD335/NKp46, NKp44, NKp30, CD226/DNAM-1 or Killer Immunoglobulin like receptors.

In one embodiment of the invention said NK cells in a cell culture medium comprising a population of NK cells may be NK cells that may be transduced with the retroviral vector particle or the virus-like particle thereof as disclosed herein to express an immunoregulatory molecule such as PD-L1, CTLA-4, LAG-3, CD39 or CD73.

In one embodiment of the invention said NK cells in a cell culture medium comprising a population of NK cells may be NK cells that may be transduced with the retroviral vector particle or the virus-like particle thereof as disclosed herein for increased or decreased expression of inhibitory receptors, such as KIR molecules, NKG2A, PD-1 or A2AR.

In one embodiment of the invention said NK cells in a cell culture medium comprising a population of NK cells may be NK cells that may be transduced with the retroviral vector particle or the virus-like particle thereof as disclosed herein to produce cytokines, such as IL-2 or IL-15.

In one embodiment of the invention said NK cells in a cell culture medium comprising a population of NK cells may be NK cells that may be transduced with the retroviral vector particle or the virus-like particle thereof as disclosed herein to express a peptide therapeutic or protein therapeutic, such as a therapeutic antibody.

In one embodiment of the invention said NK cells in a cell culture medium comprising a population of NK cells may be NK cells that may be transduced with the retroviral vector particle or the virus-like particle thereof as disclosed herein to express a protein for cell tracking, such as GFP for fluorescent tracking, or luciferase for chemiluminescent tracking with luciferin. In one embodiment of the invention the method consisting of NK cell isolation, NK cell cultivation and NK cell transduction is performed in a closed system as known by the person skilled in the art. In a further embodiment the closed system is a disposable tubing set attached to a cell processing device. In a further embodiment that said cell processing device is a CliniMACS Prodigy® (Miltenyi Biotec). In a further embodiment transduced NK cells are further cultivated in a larger volume in a second closed system.

In one embodiment of the invention said NK cells are expanded after transduction in large scale in a volume of about 200 to 1000 liters, providing clinical products of genetically modified NK cells for a large number of patients.

In one embodiment of the invention said transduced NK cells are cryopreserved. Aliquots of cryopreserved NK cells are thawed and further cultivated in said culturing process, allowing for production of transduced NK cells starting from a cryopreserved cell bank.

In one embodiment of the invention said NK cells are expanded from a single NK cell by limiting dilution for generation of a phenotypically uniform NK cell product. This uniform NK cell may be transduced with the retroviral vector particle or the virus-like particle thereof as disclosed herein.

In one embodiment of the invention said NK cells are tumor infiltrating NK cells isolated from a tumor biopsy. These isolated NK cells may be transduced with the retroviral vector particle or the virus-like particle thereof as disclosed herein.

In one embodiment of the invention said NK cells are generated from cord blood CD34+ hematopoietic progenitor cells in a cell culture process. These generated NK cells may be transduced with the retroviral vector particle or the virus-like particle thereof as disclosed herein.

In one embodiment of the invention said NK cells are generated from induced pluripotent stem cells in a cell culture process. These generated NK cells may be transduced with the retroviral vector particle or the virus-like particle thereof as disclosed herein.

In one embodiment of the invention said NK cells are isolated from blood of a donor selected for high NK cell functionality. These isolated and selected NK cells may be transduced with the retroviral vector particle or the virus-like particle thereof as disclosed herein.

In one embodiment of the invention said NK cells are isolated from cord blood. These isolated NK cells may be transduced with the retroviral vector particle or the virus-like particle thereof as disclosed herein.

EXAMPLES

Example 1: Surprisingly, Lentiviral Vector Pseudotyped with Baboon Envelope Glycoprotein (BaEV) Shows High Transduction Efficiency of Primary NK Cells when the NK Cells have been Pre-Activated For NK cell isolation from buffy coats, peripheral blood mononuclear cell (PBMC) preparation was performed by standard density-gradient centrifugation using Ficoll-Paque PLUS (GE Healthcare). NK cell isolation kit human (Miltenyi Biotec) was applied for untouched enrichment of NK cells from PBMC. Isolated NK cells were divided in three groups, activated them for different durations and transduced with BaEV pseudotyped lentiviral vectors contained GFP. All transductions were performed with 10 ng/ml vectofusin (Miltenyi Biotec) and spinoculation following manufacturer protocol. First group of NK cells were transduced immediately after isolation (No activation). Second group of NK cells were cultured in NK MACS medium (Miltenyi Biotec) containing 5% AB serum, 500 U/ml IL-2 and 10 ng/ml IL-15 for 1 day (activated in IL-2+IL-15 for 1 day) and then transduced. Third group of NK cells were culture in NK MACS medium (Miltenyi Biotec) containing 5% AB serum, 500 U/ml IL-2 and 10 ng/ml IL-15 for 2 days (activated in IL-2+IL-15 for 2 days) and then transduced. As a control for each transduced group, NK cells were culture in same condition like transduced cells except no viral vector were added (Non-transduced). Three days after transduction, non-activated NK cells showed only 2.44% of transduction (No activation, lower left panel of FIG. 1). On the other hand, NK cells groups that were cultured in NK MACS medium (Miltenyi Biotec) containing 5% AB serum, 500 U/ml IL-2 and 10 ng/ml IL-15 for 1 day and 2 days, showed 14.59% and 22.61% of GFP expression, respectively (FIG. 1, transduced, middle and right lower panel). In each group, non-transduced NK cells did not show any expression of GFP (FIG. 1, upper panels, non-transduced).

Figure 5:
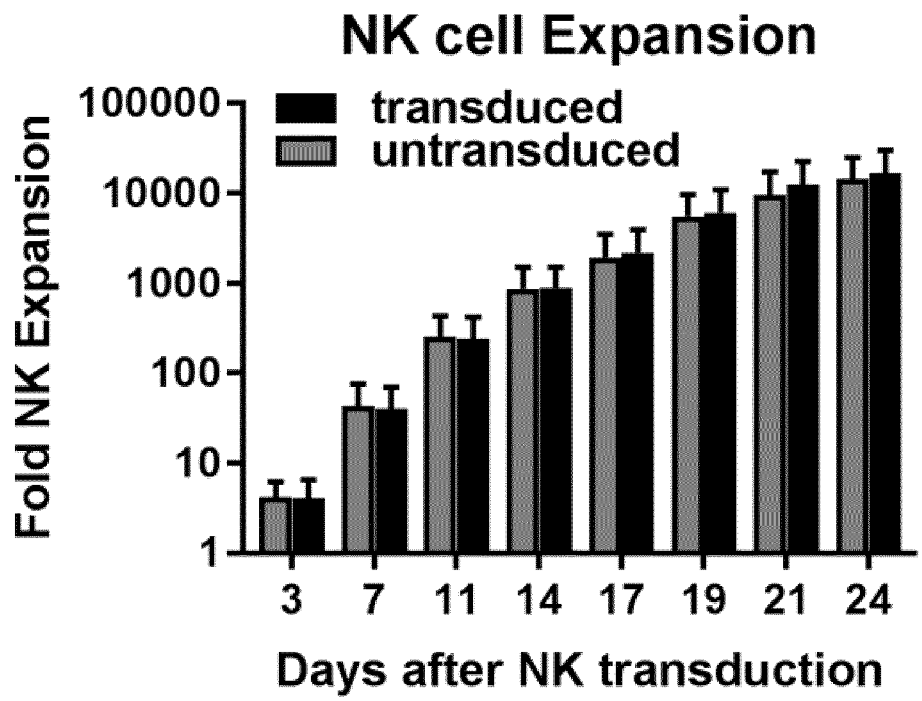
FIG. 5: Activated NK cells transduced with BaEV pseudotyped vector show the same expansion rate as untransduced NK cells, proving that the transduction itself does not induce cell death and does not affect the cell proliferation
Figure 6:
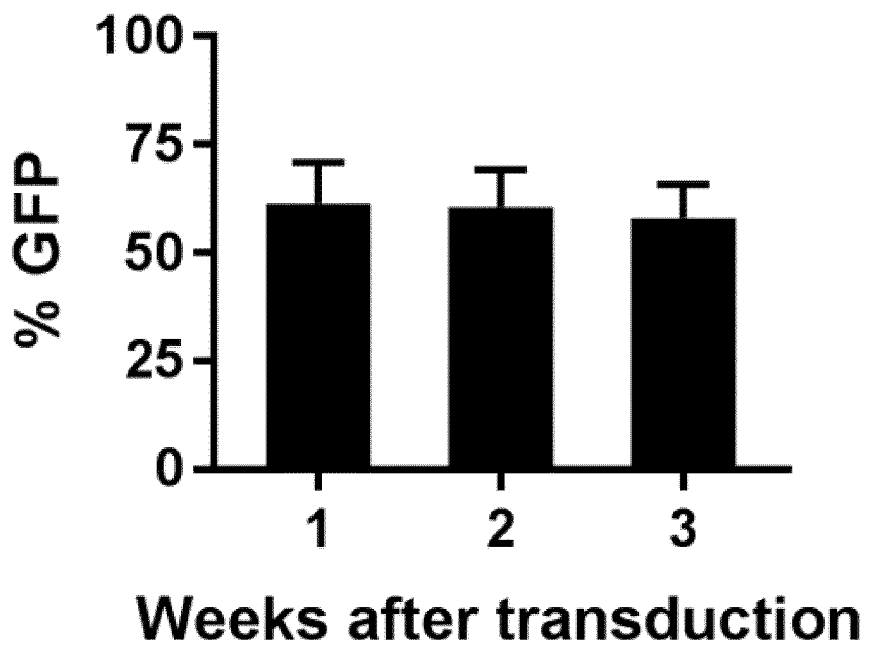
FIG. 6: Transgene expression after transduction of NK cells with BaEV pseudotyped vector is stable for long time FIG. 7 A: Activation of NK cells and the use of BaEV pseudotyping allows very high transduction rates, which makes it possible to generate NK cells with high CAR expression FIG. 7 B: Different target cells show different expression profiles for the surface marker CD19, making them suitable targets for functional testing of CD19-CAR expressing NK cells FIG. 7 C: The transduction method allows the generation of CD19-CAR expressing NK cells with an unchanged high cytotoxic potential demonstrated by killing of K562 cells, and a significantly increased CD19-specific cytotoxic activity, demonstrated by killing of CD19 positive RS4; 11 and Raji cells

Example 2: Transduction of Activated NK Cells with BaEV is Significantly Higher than with VSV-G, Stable Over Long Time, and does not Induce Cell Death Primary NK cells were isolated as described in Example 1, resulting in pure CD3$^-$ and CD56$^+$ NK cells (FIG. 2 A). T cells were isolated from the same blood samples using MicroBeads against CD4 and MicroBeads against CD8 from Miltenyi according to the user manual, resulting in pure CD3 positive T cells (FIG. 2 A) After isolation, NK cells were activated for 2 days in NK MACS medium with 5% AB serum, 10 ng/mL IL-15 and 500 U/mL IL-2. After isolation, T cells were activated for 2 days in TexMACS medium with 200 U/mL IL-2 and T Cell Transact human from Miltenyi, according to the user manual. Then, the activated primary T cells and NK cells, as well as NK-92 cell line, were transduced with supernatants containing lentiviral vectors coding for GFP expression, either pseudotyped with VSV-G envelope or pseudotyped with BaEV. Three days after transduction with VSV-G pseudotyped viral particles, NK cells showed only around 2% GFP expression even at high virus titers, whereas T cells showed a high GFP expression of around 77% under the same condition (FIG. 2 B). This observation confirms that NK cell transduction with VSV-G pseudotyped lentiviral vectors is inefficient, while it works for other cell types including T cells. Surprisingly, 3 days after transduction of the NK cell line NK-92 with BaEV pseudotyped viral vector, high GFP expression of nearly 100% was observed, while the GFP expression with VSV-G, similar to primary NK cells, was inefficient (FIG. 2 C). NK-92 cells were maintained under activating conditions in NK MACS medium containing 200 U/mL IL-2. In line with the observation on NK-92, a surprisingly high rate of 60% of activated primary NK cells expressed GFP when transduction with BaEV pseudotyped vector was applied, reaching comparable transduction rates as T cells (FIG. 2 D). Importantly, expansion rates, meaning the increase in cell numbers over time, was comparable for untransduced NK cells and NK cells transduced with the BaEV pseudotyped, indicating that the transduction method does not induce cell death nor does it affect the proliferation of the NK cells (FIG. 5). This is different from other methods for genetic modification, such as electroporation, where the treatment causes high degrees of cell death. In addition, other methods for genetic modification, such as electroporation, only allow transient expression of the transgene. Of note, after transduction with the BaEV pseudotyped lentiviral vector the constantly high percentage of NK cells that expressed the transgene was stable over weeks (FIG. 6).

Example 3: Surprisingly, Short Activation of NK Cells with IL-33 Allows Higher Transduction Rates of NK Cells than without IL-33

Figure 3:
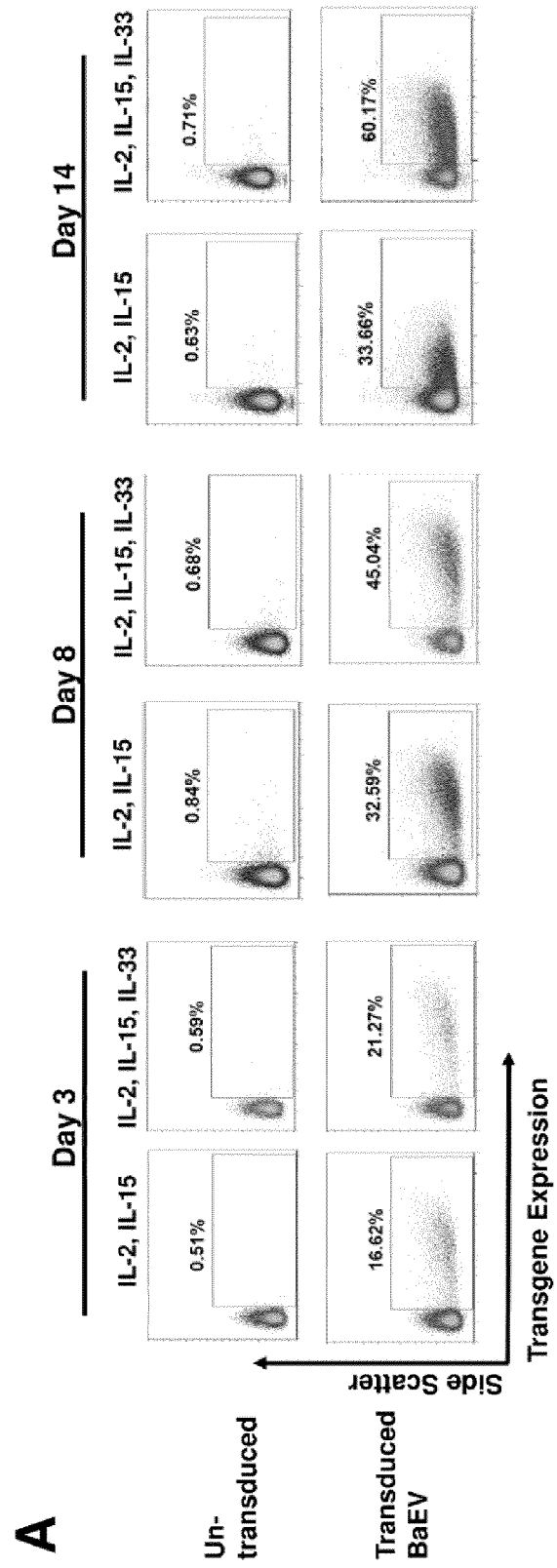
FIG. 3 B: Similar as with BaEV pseudotyped vector, short activation of NK cells with IL-33 increases the transduction rates of NK cells even when VSV-G pseudotyped lentiviral vector is used
Figure 3:
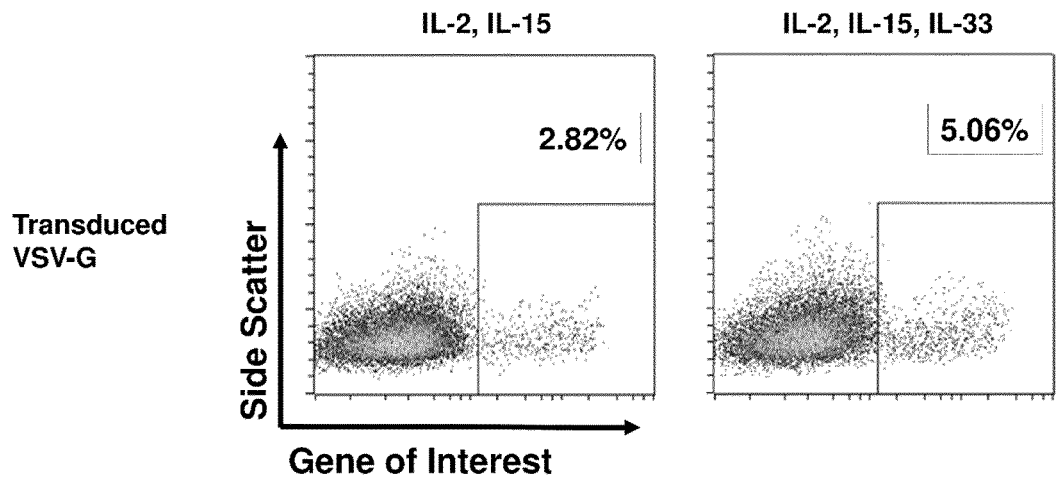

Primary NK cells were isolated as described in Example 1. Purified NK cells were activated for 2 days in NK MACS medium with 5% AB serum containing either IL-2 (500 U/ml) and IL-15 (10 ng/ml), or IL-2 (500 U/ml), IL-15 (10 ng/ml) and IL-33 (30 U/ml). On day 2, cells were transduced with lentiviral vectors pseudotyped with baboon (BaEV) (FIG. 3A) or VSV-G (FIG. 3B) envelope containing a gene of interest. Transductions were done as described in example 1. Untransduced cells were cultured in the same condition like transduced cells. After transduction, the cells were cultured in medium without IL-33. Transgene expression in transduced NK cells was detected with a specific monoclonal antibody directed against the product of the gene of interest on day 3, day 8, and day 14, after transduction. The transgene expression on day 3 after transduction, without IL-33 was 16.62 and with IL-33 was 21.27%, respectively (FIG. 3A, lower left panels). The transgene expression on day 8 after transduction, without IL-33 was 32.59% and with IL-33 was 45.03%, respectively (FIG. 3A, middle panels). On day 14 after transduction, the transgene expression was 33.66% without IL-33 and 60.17% with IL-33 (FIG. 3A, right lower panels). This result suggests that pre-stimulation of NK cells with IL-33 has an additive effect on transduction. Untransduced NK cells showed very low level of antibody staining (less than 1%, FIG. 3A, upper panels). Although lentiviral vector pseudotyped with VSV-G envelope showed significantly lower transduction efficiency compared to baboon pseudotyped vector, however the additive effect of IL-33 is still significant (FIG. 3B).

Figure 4:
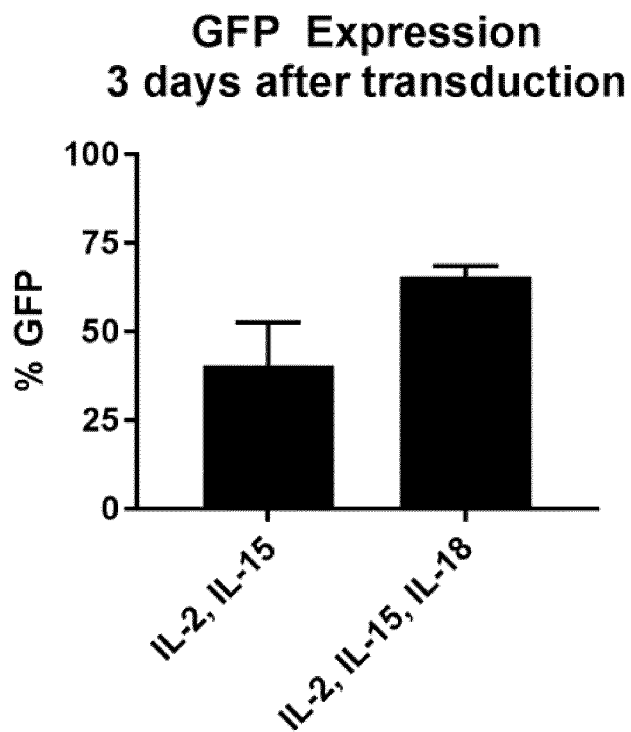
FIG. 4: Activation of NK cells with IL-18 increased the transduction rate of NK cells in a similar way as IL-33

Example 4: IL-18 Increased NK Cell Transduction Rates, Similar to IL-33, Implying a General Role for IL-1 Family Cytokines From 3 different donors primary NK cells were isolated as described in Example 1. After isolation, NK cells from the same donors were activated for 2 days in NK MACS medium with 5% AB serum, 10 ng/mL IL-15 and 500 U/mL IL-2 either with the addition of 20 ng/mL IL-18 or without IL-18. Then, the activated primary NK cells were transduced with lentiviral vector coding for GFP, pseudotyped with BaEV. After transduction, the cells were cultured in culture medium without IL-18 but with IL-2 and IL-15. Three days after transduction, NK cells showed a mean GFP expression of 40% when pre-activated without IL-18, while NK cells from the same donors showed a significant higher GFP expression of 66% when pre-activated with IL-18 (FIG. 4).

Example 5: The Use of BaEV Pseudotyped Lentiviral Vector Make it Possible to Efficiently Transduce Activated NK Cells with a CD19 CAR for Specific Killing of CD19 Positive Target Cells CAR expressing T cells led to very positive results in clinical trials for the treatment of CD19 positive B cell leukemia. Since CAR NK cells may be an alternative to CAR T cells, we transduced NK cells with a CAR against CD19, as one exemplary application for NK cell transduction. Primary NK cells were isolated from 4 different donors as described in Example 1. After isolation, NK cells from the same donors were activated for 2 days in NK MACS medium with 5% AB serum, 10 ng/mL IL-15 and 500 U/mL IL-2. Then, the activated primary NK cells were transduced with lentiviral vector coding for CD19-CAR. The used "CD19B" CAR construct and it is expression in T cells after transduction with VSV-G was described before (Schneider et al. 2017). For transduction of NK cells a lentiviral vector pseudotyped with BaEV was generated for this construct and used. Seven days after transduction the CAR expression and NK cell cytotoxicity were analyzed. In detail, after incubation of NK cells for 48 h in serum free culture medium, CD19-CAR expression was determined by binding of recombinant human CD19 Fc (R&D Systems), 25 µg/mL for 30 min, and detection via flow cytometry using a murine APC conjugated mAb against Fc (Miltenyi Biotec). On average, the expression of the CD19-CAR was 70% among NK cells from different donors, with some donors reaching a transduction rate of 90% (FIG. 7 A). Target cell killing of different target cell lines was analyzed by a flow cytometry-based assay. Target cells were labeled with CellTrace Violet (Life Technologies) and $2\times10^3$ cells per well were seeded in 96-well round-bottom plates. Then, medium as a control or NK cells at different NK-to-target ratios were added. After 24 h the CellTrace Violete positive target cells were quantified by flow cytometry. The difference between viable target cells in samples with NK cells and corresponding samples without NK cells was defined as killed targets. K562 cells don't express CD19 (FIG. 7 B), but they can be considered a standard target to test NK cells general cytotoxic potential due to their sensitivity to NK cells natural cytotoxicity. As expected, CAR NK cells and untransduced NK cells both killed K562 cells very efficiently in the very same dose-dependent manner, proving that the CD19-independent natural cytotoxicity is not affected by the transduction (FIG. 7 C). In contrast to K562 cells, RS4; 11 cells express CD19 (FIG. 7 B), but they are completely insensitive to NK cell natural cytotoxicity. Consequently, untransduced NK cells were unable to kill RS4; 11 cells, whereas CD19-CAR NK cells killed RS4; 11 as efficiently as K562 cells, demonstrating the high functionality and specificity of the used CD19 CAR (FIG. 7 B). Raji cells are CD19 positive (FIG. 7 B), but different to RS4; 11, they are sensitive to activated NK cells natural cytotoxicity, although to a lower degree as K562 cells. Therefore, untransduced NK cells were already able to kill Raji cells in a dose dependent manner, nevertheless the killing of Raji cells by CD19 CAR NK cells was significantly higher, implying an additive effect of the CD-19 specific killing. In conclusion, transduction of NK cells with a BaEV pseudotyped lentiviral vector made it possible to efficiently generate CD19 CAR expressing NK cells with improved, CD19 specific killing of leukemic target cells.

Example 6: Activated but not Naive NK Cells Expressed the Receptor for Baboon Envelope ASCT2

NK cells were activated by growing them in NK MACS medium (Miltenyi Biotec GmbH) with IL-2 and IL-15 for 2 days. Both naive and activated cells were lysed in RIPA lysis buffer and subjected to westernblot analysis using antibody against ASCT2. This result showed that the receptor for baboon envelope, ASCT2, is only expressed after NK cell activation (FIG. 8) but not in the naive NK cells suggesting that the NK cells need to be activated to be transduced with baboon pseudotyped lentiviral vector.

Example 7: Proliferative but not the Quiescent NK Cells are Transducible

Figure 10:
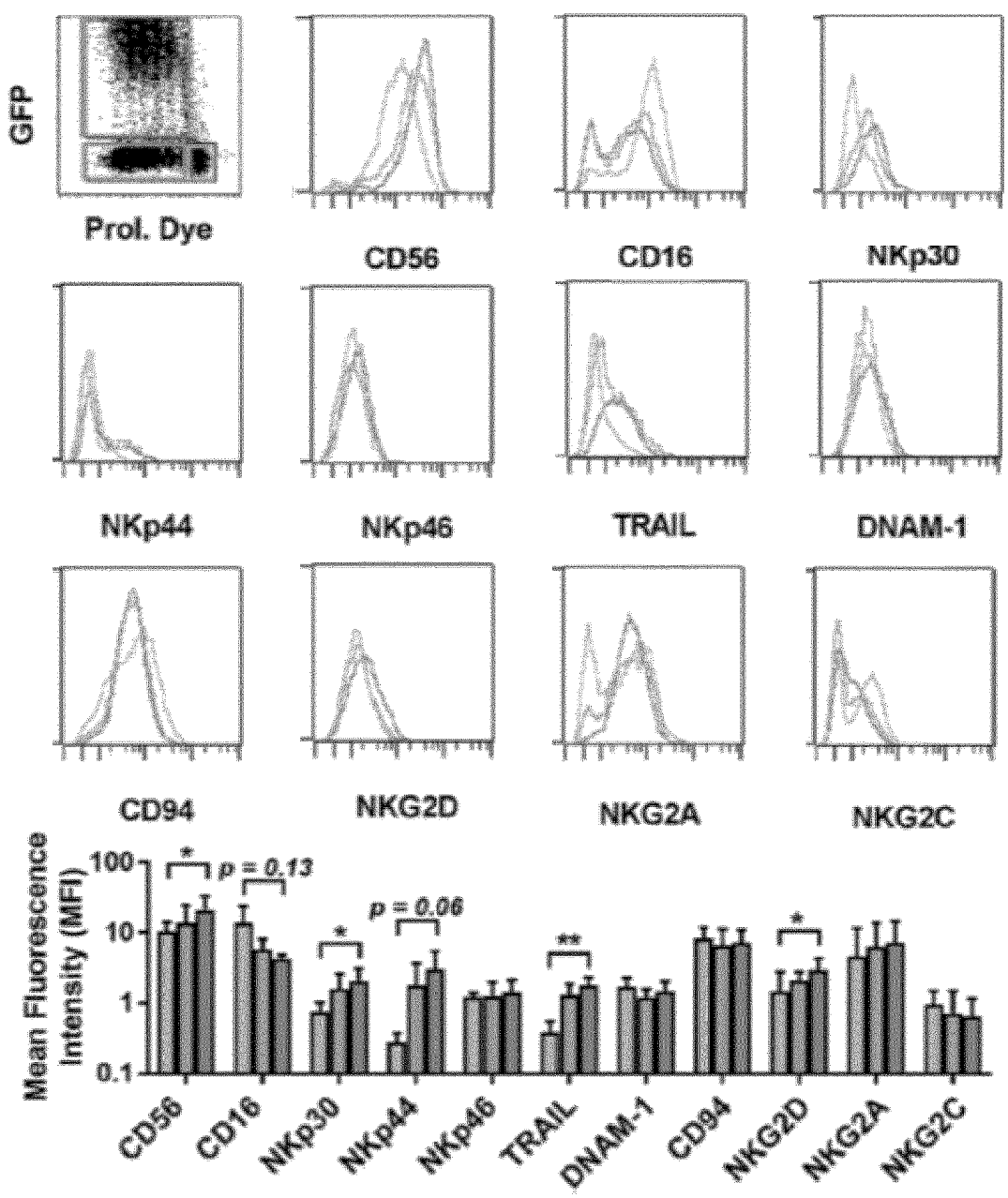
FIG. 10: Comparison of several NK cell receptors among proliferated and transduced, proliferative but non-transduced and quiescent subset of NK cells showed that the quiescent NK cells had a significant different phenotype than proliferative NK cells. Proliferative cells were more CD56 bright with a tendency of lower CD16 expression, higher expression of the activating receptors NKp30, NKp44 and NKG2D, as well as higher expression of TRAIL and NKG2A FIG. 11 A-B: Marker screening of cell surface protein of proliferated and quiescent subset of NK cells. NK cells from 5 donors were used to analyzed for 371 surface markers by flow cytometry. Direct comparison to quiescent NK cells, proliferative and GFP positive NK cells expressed 32 markers at a higher and 5 markers at a lower level (FIG. 11 A). Most obvious marker for the proliferative and transducible NK cell subset was the absence of CX3CR1 expression and a high frequency of cells strongly expressing TRAIL (FIGS. 11A and 11 B).
Figure 13:
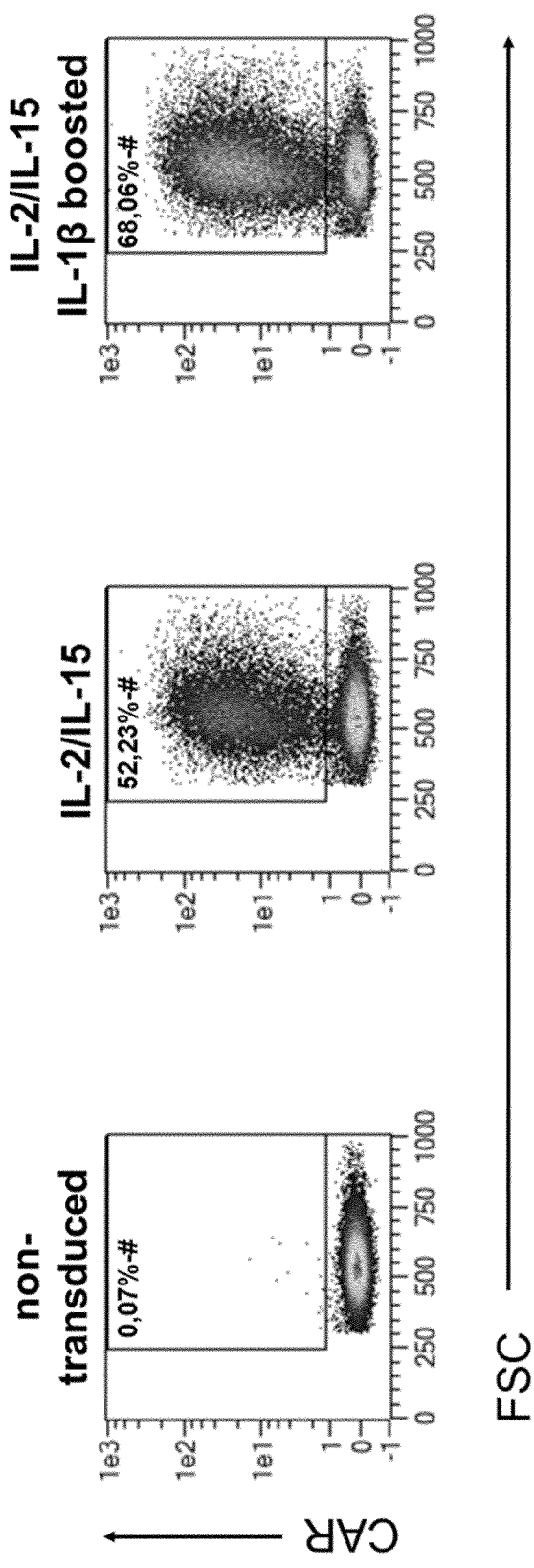
FIG. 13: Expression of a chimeric antigen receptor (CAR) ten days after lentiviral transduction of NK cells using a BaEV-pseudotyped lentiviral vector and IL-1beta

NK cells were labeled with proliferation dye, washed extensively and then transduced with baboon pseudotyped lentiviral vector containing GFP. Cell proliferation and transduction were determined 4 days after start proliferation and transduction by flow cytometry. Results suggest that only the proliferative but not the quiescent NK cells are transducible with baboon pseudotyped lentiviral vector (FIG. 9A). The GFP transduced NK cells were stained with anti-CD56 antibody and gated the three group of NK cell (GFP+, GFP-proliferated, quiescent) to determine the level of CD56 expression (FIG. 9B). All of the proliferated and transduced NK cells were CD56$^{bright}$ whereas non-transduced quiescent NK cells were CD56$^{dim}$ suggesting that the CD56$^{dim}$ NK subset were not proliferative and non-transducible. Next, we further compared other NK cell receptors among proliferated and transduced, proliferative but non-transduced and quiescent subset of NK cells (FIG. 10). NK cells were labeled with proliferation dye, washed extensively and then transduced with baboon pseudotyped lentiviral vector containing GFP. Day 4 after transduction, cells were stained with monoclonal antibody against different NK cells receptors and expressions were determined using flow cytometry. The expression of commonly known NK cell markers among the different subsets are shown (FIG. 10). Expression of NKp46, DNAM-1, CD94 and NKG2C were comparable between all the different NK cell subsets. Within the fraction of proliferative cells, the difference of different NK cell marker expression between GFP$^+$ and GFP$^-$ cells were not significant. However, according to the expression of several markers, quiescent NK cells had a significant different phenotype than proliferative NK cells. Proliferative cells were more CD56 bright with a tendency of lower CD16 expression, higher expression of the activating receptors NKp30, NKp44 and NKG2D, as well as higher expression of TRAIL and NKG2A (FIG. 10).

Example 8: CX3CRP1$^{neg}$ NK Cells Subset is Highly Proliferative and Transducible NK cells from 5 donors were used to analyzed for 371 surface markers by flow cytometry. The differences between the marker profiles of quiescent NK cells and proliferative NK cells were analyzed, which were further divided in the GFP expressing population and a GFP negative population. From the screening, markers distinguished best between the quiescent NK cells that don't express GFP and the proliferative NK cells that can be transduced and express GFP were determined. Overall, in direct comparison to quiescent NK cells, proliferative and GFP positive NK cells expressed 32 markers at a higher and 5 markers at a lower level (FIG. 11 A). Out of these markers, some did not only differ in the expression level but also in the frequency of NK cells that express the specific marker. Most obvious was the absence of CX3CR1 expression and a high frequency of cells strongly expressing TRAIL among the proliferative and GFP positive NK cells (FIG. 11 B).

Example 9: CX3CR1$^{neg}$ NK Cells Subset are Highly Transducible with Baboon Pseudotyped Lentiviral Vector and could be Used as a Marker From the surface molecules that correlated best with proliferation and transduction, CX3CR1 was selected for further investigation to test whether this marker can directly discriminate between NK cells subsets with different capabilities for proliferation and transduction. Different NK cell subsets were separated based on their CX3CR1 expression using MCAS sorting prior to transduction and culture. Without sorting, the expression of CX3CR1 among blood derived NK cells from different donors was 86%, meaning that only a small fraction of around 14% of all NK cells did not express CX3CR1 (FIG. 5A). After sorting, the mean frequency of CX3CR1$^{neg}$ NK cells could be reduced to 2% by enrichment for CX3CR1, while depletion for the marker on the other hand led to 91% CX3CR1$^{neg}$ NK cells (FIG. 12A). Shortly after cultivation and transduction of the differently sorted NK cell fractions, we observed significant differences regarding transgene expression and rate of proliferation (FIG. 12B, 12C). Among the unsorted fraction the rates of proliferation and GFP expression were 28% and 21%, respectively. At the same time, the CX3CR1-enriched fraction with a marginal content of CX3CR1 negative cells contained only 11% proliferating and 7% GFP positive cells. Impressively, among the CX3CR1-depleted fraction with a high starting frequency of CX3CR1$^{neg}$ NK cells already 81% were proliferating and 69% were GFP positive. Even within the CX3CR1-enriched fraction, proliferation and GFP expression was mainly observed in the remaining CX3CR1$^{neg}$ cells (FIG. 12C). Altogether, the experiments identified a subset of highly proliferative NK cells that can be efficiently transduced with BaEV pseudotyped LV. This NK cell subset could be clearly defined by the absence of CX3CR1 expression and this characteristic could be used for pre-enrichment for transducible NK cells.

Example 10: IL-1Beta Increased NK Cell Transduction Rates

Fresh NK cells were isolated from peripheral blood mononuclear cells (PBMCs) and stimulated with IL-2/IL-15 or IL-2/IL-15/IL-1β (IL-1beta) for three days. On day 2 after activation, the lymphocytes were transduced with a multiplicity of infection (MOI) of 3. The following day, the cells were washed and expansion was continued for an additional 7 days in the presence of IL-2/IL-15. To detect the frequency of genetically modified NK cells, cells were labelled with a biotinylated anti-idiotpye antibody which targets specifically the scFv domain of the CAR. Detection of the biotin conjugate was performed using an anti-biotin-PE secondary mAb labeling. Percentage of positive cells is indicated in each dot plot showing that fresh NK cells stimulated with IL-2, IL-15 and IL-1beta result in superior transduction rates compared to IL-2/IL-15 without IL-1beta (68% vs 52%). Results are representative for 3 independent experiments.

REFERENCES

Aiuti, A. et al., 2009. Gene therapy for immunodeficiency due to adenosine deaminase deficiency. *N Engl J Med*, 360(5), pp. 447-458. Available at: http://www.ncbi.nlm-.nih.gov/pubmed/19179314.

Aiuti, A. & Roncarolo, M. G., 2009. Ten years of gene therapy for primary immune deficiencies. *Hematology. American Society of Hematology. Education Program*, pp. 682-9. Available at: http://www.ncbi.nlm.nih.gov/pubmed/20008254.

Apel, M. et al., 2013. Integrated Clinical Scale Manufacturing System for Cellular Products Derived by Magnetic Cell Separation, Centrifugation and Cell Culture. *Chemie Ingenieur Technik*, 85(1-2), pp. 103-110. Available at: http://doi.wiley.com/10.1002/cite.201200175 [Accessed Dec. 6, 2013].

Bai, L.-Y. et al., 2015. BX795, a TBK1 inhibitor, exhibits antitumor activity in human oral squamous cell carcinoma through apoptosis induction and mitotic phase arrest. *European journal of pharmacology*, 769, pp. 287-96. Available at: http://www.ncbi.nlm.nih.gov/pubmed/26607461.

Childs, R. W. & Berg, M., 2013. Bringing natural killer cells to the clinic: ex vivo manipulation. *Hematology/the Edu-* cation Program of the American Society of Hematology. *American Society of Hematology. Education Program*, 2013, pp. 234-46. Available at: http://www.ncbi.nlm.nih.gov/pubmed/24319186.

Childs, R. W. & Carlsten, M., 2015. Therapeutic approaches to enhance natural killer cell cytotoxicity against cancer: the force awakens. *Nature reviews. Drug discovery*, (May). Available at: http://www.ncbi.nlm.nih.gov/pubmed/26000725 [Accessed May 27, 2015].

Klingemann, H., 2014. Are natural killer cells superior CAR drivers? *OncoImmunology*, 3(4), p.e28147. Available at: http://www.tandfonline.com/doi/abs/10.4161/onci.28147.

Leung, W., 2014. Infusions of allogeneic natural killer cells as cancer therapy. *Clinical cancer research: an official journal of the American Association for Cancer Research*, 20(13), pp. 3390-400. Available at: http://www.ncbi.nlm.nih.gov/pubmed/24987108 [Accessed Sep. 19, 2014].

Miller, J. S. et al., 2005. Successful adoptive transfer and in vivo expansion of human haploidentical NK cells in patients with cancer. *Blood*, 105(8), pp. 3051-7. Available at: http://www.ncbi.nlm.nih.gov/pubmed/15632206.

Montini, E. et al., 2009. The genotoxic potential of retroviral vectors is strongly mediated by vector design and integration site selection in a mouse model of HSC gene therapy. *The Journal of Clinical Investigation*, 119(4), pp. 964-975.

Papayannakos, C. & Daniel, R., 2013. Understanding lentiviral vector chromatin targeting: working to reduce insertional mutagenic potential for gene therapy. *Gene therapy*, 20(6), pp. 581-8. Available at: http://www.ncbi.nlm.nih.gov/pubmed/23171920.

Pillai, S. et al., 2015. Tank binding kinase 1 is a centrosome-associated kinase necessary for microtubule dynamics and mitosis. *Nature Communications*, 6, p. 10072. Available at: http://www.nature.com/doifinder/10.1038/ncomms10072.

Rubnitz, J. E. et al., 2010. NKAML: a pilot study to determine the safety and feasibility of haploidentical natural killer cell transplantation in childhood acute myeloid leukemia. *Journal of clinical oncology: official journal of the American Society of Clinical Oncology*, 28(6), pp. 955-9. Available at: http://www.ncbi.nlm.nih.gov/pubmed/20085940.

Schneider, D. et al., 2017. A tandem CD19/CD20 CAR lentiviral vector drives on-target and off-target antigen modulation in leukemia cell lines. *Journal for immunotherapy of cancer*, 5(1), p. 42. Available at: http://jitc.biomedcentral.com/articles/10.1186/s40425-017-0246-1.

Suerth, J. D. et al., 2015. Efficient generation of gene-modified human natural killer cells via alpharetroviral vectors. *Journal of molecular medicine* (Berlin, Germany). Available at: http://link.springer.com/10.1007/s00109-015-1327-6.

Sutlu, T. et al., 2012 Inhibition of intracellular antiviral defense mechanisms augments lentiviral transduction of human natural killer cells: implications for gene therapy. *Human gene therapy*, 23(10), pp. 1090-100. Available at: http://www.ncbi.nlm.nih.gov/pubmed/22779406\nhttp://www.pubmedcentral.nih.gov/articlerender.fcgi?artid=PMC3472531.

---

The invention claimed is:

1. A method for transducing human NK cells with a nucleic acid, the method comprising:
   a) obtaining a cell population that comprises NK cells,
   b) activating a plurality of NK cells in the population comprising contacting the NK cells with one or a combination of cytokines, including interleukin-2 (IL-2) and/or interleukin-15 (IL-15), and then
   c) contacting the activated NK cells with a plurality of pseudotyped retroviral vectors each containing said nucleic acid,
   wherein the pseudotyped retroviral vectors comprise either:
   (1) a chimeric envelope glycoprotein that comprises a fusion of the transmembrane and extracellular domain of a baboon endogenous retrovirus (BaEV) envelope glycoprotein with the cytoplasmic tail domain of a murine leukemia virus (MLV) envelope glycoprotein; or
   (2) a BaEV envelope glycoprotein that has been recombinantly modified from wild type BaEV envelope glycoprotein by removing the glycoprotein's fusion inhibitory R peptide;
   wherein contacting said activated NK cells with said vectors transduces said nucleic acid into the activated NK cells.

2. The method according to claim 1, wherein the NK cells are negative for CX3C chemokine receptor 1 (CX3CR1).

3. The method according to claim 1, wherein said pseudotyped retroviral vector comprises a chimeric envelope glycoprotein that comprises the transmembrane and extracellular domains of a baboon endogenous retrovirus (BaEV) envelope glycoprotein fused with the cytoplasmic tail domain of a murine leukemia virus (MLV) envelope glycoprotein.

4. The method according to claim 1, wherein said pseudotyped retroviral vector comprises a modified BaEV envelope glycoprotein that has an amino acid sequence at least 80% identical to the amino acid sequence of wild-type BaEV envelope glycoprotein, recombinantly altered to remove the fusion inhibitory R peptide.

5. The method according to claim 1, wherein said combination of cytokines includes an IL-1 family cytokine.

6. The method according to claim 5, wherein said IL-1 family cytokine is IL-18, IL-33, or IL-1 beta.

7. The method according to claim 1, wherein the transduction efficiency of the NK cells by said pseudotyped retroviral vector is at least 50%, wherein transduction efficiency is defined as the percentage of NK cells in the cell population produced following step (c) that express a protein encoded in the vector.

8. The method according to claim 1, wherein said retroviral vector is a lentiviral vector.

9. The method according to claim 1, performed as an automated process in a closed system.

10. The method of claim 1, further comprising administering the transduced NK cells to a subject in need thereof.

11. A method for improving efficiency of transducing a nucleic acid into human natural killer (NK) cells; wherein the transducing comprises contacting the NK cells with a retroviral vector containing said nucleic acid, wherein the method is improved:
    (a) by using a pseudotyped retroviral vector to transduce the NK cells, wherein the pseudotyped retroviral vector comprises either: (1) a chimeric envelope glycoprotein in which the transmembrane and extracellular domain of a baboon endogenous retrovirus (BaEV) envelope glycoprotein is recombinantly fused the cytoplasmic tail domain of a murine leukemia virus (MLV) envelope glycoprotein; or (2) a BaEV envelope glycoprotein that has been recombinantly modified to remove the glycoprotein's fusion inhibitory R peptide; and
    (b) by activating the NK cells comprising contacting the NK cells with one or a combination of cytokines, including interleukin-2 (IL-2) and/or interleukin-15 (IL-15) 15 before they are contacted with the pseudotyped retroviral vector; thereby improving the efficiency of the transducing of the nucleic acid into the NK cells.

12. The method of claim 11, wherein the combination of cytokines includes an IL-1 family cytokine.

13. The method of claim 12, wherein the IL-1 family cytokine is IL-18, IL-33, or IL-1 beta.

14. The method of claim 11, wherein the method is further improved: by using NK cells that are negative for expression of CX3C chemokine receptor 1 (CX3CR1).

15. The method of claim 11, wherein the activating results in at least a 5-fold improvement of efficiency of transduction of the nucleic acid by the pseudotyped retroviral vector into the NK cells.

16. The method of claim 1, wherein the nucleic acid transduced into the NK cells encodes a chimeric antigen receptor (CAR), thereby producing CAR-NK cells.

* * * * *

SEQUENCE LISTING

```
<160> NUMBER OF SEQ ID NOS: 4

<210> SEQ ID NO 1
<211> LENGTH: 563
<212> TYPE: PRT
<213> ORGANISM: Artificial sequence
<220> FEATURE:
<223> OTHER INFORMATION: wild-type BaEV envelope glycoprotein

<400> SEQUENCE: 1

Met Gly Phe Thr Thr Lys Ile Ile Phe Leu Tyr Asn Leu Val Leu Val
1               5                   10                  15

Tyr Ala Gly Phe Asp Asp Pro Arg Lys Ala Ile Glu Leu Val Gln Lys
            20                  25                  30

Arg Tyr Gly Arg Pro Cys Asp Cys Ser Gly Gly Gln Val Ser Glu Pro
        35                  40                  45

Pro Ser Asp Arg Val Ser Gln Val Thr Cys Ser Gly Lys Thr Ala Tyr
    50                  55                  60

Leu Met Pro Asp Gln Arg Trp Lys Cys Lys Ser Ile Pro Lys Asp Thr
65                  70                  75                  80

Ser Pro Ser Gly Pro Leu Gln Glu Cys Pro Cys Asn Ser Tyr Gln Ser
                85                  90                  95

Ser Val His Ser Ser Cys Tyr Thr Ser Tyr Gln Gln Cys Arg Ser Gly
            100                 105                 110

Asn Lys Thr Tyr Tyr Thr Ala Thr Leu Leu Lys Thr Gln Thr Gly Gly
        115                 120                 125

Thr Ser Asp Val Gln Val Leu Gly Ser Thr Asn Lys Leu Ile Gln Ser
    130                 135                 140

Pro Cys Asn Gly Ile Lys Gly Gln Ser Ile Cys Trp Ser Thr Thr Ala
```

```
        145                 150                 155                 160
Pro Ile His Val Ser Asp Gly Gly Pro Leu Asp Thr Thr Arg Ile
                    165                 170                 175
Lys Ser Val Gln Arg Lys Leu Glu Glu Ile His Lys Ala Leu Tyr Pro
                    180                 185                 190
Glu Leu Gln Tyr His Pro Leu Ala Ile Pro Lys Val Arg Asp Asn Leu
                    195                 200                 205
Met Val Asp Ala Gln Thr Leu Asn Ile Leu Asn Ala Thr Tyr Asn Leu
                210                 215                 220
Leu Leu Met Ser Asn Thr Ser Leu Val Asp Asp Cys Trp Leu Cys Leu
225                 230                 235                 240
Lys Leu Gly Pro Pro Thr Pro Leu Ala Ile Pro Asn Phe Leu Leu Ser
                    245                 250                 255
Tyr Val Thr Arg Ser Ser Asp Asn Ile Ser Cys Leu Ile Ile Pro Pro
                    260                 265                 270
Leu Leu Val Gln Pro Met Gln Phe Ser Asn Ser Ser Cys Leu Phe Ser
                    275                 280                 285
Pro Ser Tyr Asn Ser Thr Glu Glu Ile Asp Leu Gly His Val Ala Phe
                    290                 295                 300
Ser Asn Cys Thr Ser Ile Thr Asn Val Thr Gly Pro Ile Cys Ala Val
305                 310                 315                 320
Asn Gly Ser Val Phe Leu Cys Gly Asn Asn Met Ala Tyr Thr Tyr Leu
                    325                 330                 335
Pro Thr Asn Trp Thr Gly Leu Cys Val Leu Ala Thr Leu Leu Pro Asp
                    340                 345                 350
Ile Asp Ile Ile Pro Gly Asp Glu Pro Val Pro Ile Pro Ala Ile Asp
                355                 360                 365
His Phe Ile Tyr Arg Pro Lys Arg Ala Ile Gln Phe Ile Pro Leu Leu
                    370                 375                 380
Ala Gly Leu Gly Ile Thr Ala Ala Phe Thr Thr Gly Ala Thr Gly Leu
385                 390                 395                 400
Gly Val Ser Val Thr Gln Tyr Thr Lys Leu Ser Asn Gln Leu Ile Ser
                    405                 410                 415
Asp Val Gln Ile Leu Ser Ser Thr Ile Gln Asp Leu Gln Asp Gln Val
                    420                 425                 430
Asp Ser Leu Ala Glu Val Val Leu Gln Asn Arg Arg Gly Leu Asp Leu
                435                 440                 445
Leu Thr Ala Glu Gln Gly Gly Ile Cys Leu Ala Leu Gln Glu Lys Cys
                450                 455                 460
Cys Phe Tyr Val Asn Lys Ser Gly Ile Val Arg Asp Lys Ile Lys Thr
465                 470                 475                 480
Leu Gln Glu Glu Leu Glu Arg Arg Lys Asp Leu Ala Ser Asn Pro
                    485                 490                 495
Leu Trp Thr Gly Leu Gln Gly Leu Leu Pro Tyr Leu Leu Pro Phe Leu
                    500                 505                 510
Gly Pro Leu Leu Thr Leu Leu Leu Leu Thr Ile Gly Pro Cys Ile
                515                 520                 525
Phe Asn Arg Leu Thr Ala Phe Ile Asn Asp Lys Leu Asn Ile Ile His
                    530                 535                 540
Ala Met Val Leu Thr Gln Gln Tyr Gln Val Leu Arg Thr Asp Glu Glu
545                 550                 555                 560
Ala Gln Asp
```

```
<210> SEQ ID NO 2
<211> LENGTH: 4
<212> TYPE: PRT
<213> ORGANISM: Artificial sequence
<220> FEATURE:
<223> OTHER INFORMATION: tyrosine endocytosis signal
<220> FEATURE:
<221> NAME/KEY: misc_feature
<222> LOCATION: (2)..(3)
<223> OTHER INFORMATION: Xaa can be any naturally occurring amino acid

<400> SEQUENCE: 2

Tyr Xaa Xaa Leu
1

<210> SEQ ID NO 3
<211> LENGTH: 546
<212> TYPE: PRT
<213> ORGANISM: Artificial sequence
<220> FEATURE:
<223> OTHER INFORMATION: modified BaEV envelope glycoprotein wherein the
      cytoplasmic tail domain is devoid of the fusion inhibitory R
      peptide

<400> SEQUENCE: 3

Met Gly Phe Thr Thr Lys Ile Ile Phe Leu Tyr Asn Leu Val Leu Val
1               5                   10                  15

Tyr Ala Gly Phe Asp Asp Pro Arg Lys Ala Ile Glu Leu Val Gln Lys
            20                  25                  30

Arg Tyr Gly Arg Pro Cys Asp Cys Ser Gly Gly Gln Val Ser Glu Pro
        35                  40                  45

Pro Ser Asp Arg Val Ser Gln Val Thr Cys Ser Gly Lys Thr Ala Tyr
    50                  55                  60

Leu Met Pro Asp Gln Arg Trp Lys Cys Lys Ser Ile Pro Lys Asp Thr
65                  70                  75                  80

Ser Pro Ser Gly Pro Leu Gln Glu Cys Pro Cys Asn Ser Tyr Gln Ser
                85                  90                  95

Ser Val His Ser Ser Cys Tyr Thr Ser Tyr Gln Gln Cys Arg Ser Gly
            100                 105                 110

Asn Lys Thr Tyr Tyr Thr Ala Thr Leu Leu Lys Thr Gln Thr Gly Gly
        115                 120                 125

Thr Ser Asp Val Gln Val Leu Gly Ser Thr Asn Lys Leu Ile Gln Ser
    130                 135                 140

Pro Cys Asn Gly Ile Lys Gly Gln Ser Ile Cys Trp Ser Thr Thr Ala
145                 150                 155                 160

Pro Ile His Val Ser Asp Gly Gly Gly Pro Leu Asp Thr Thr Arg Ile
                165                 170                 175

Lys Ser Val Gln Arg Lys Leu Glu Glu Ile His Lys Ala Leu Tyr Pro
            180                 185                 190

Glu Leu Gln Tyr His Pro Leu Ala Ile Pro Lys Val Arg Asp Asn Leu
        195                 200                 205

Met Val Asp Ala Gln Thr Leu Asn Ile Leu Asn Ala Thr Tyr Asn Leu
    210                 215                 220

Leu Leu Met Ser Asn Thr Ser Leu Val Asp Asp Cys Trp Leu Cys Leu
225                 230                 235                 240

Lys Leu Gly Pro Pro Thr Pro Leu Ala Ile Pro Asn Phe Leu Leu Ser
                245                 250                 255

Tyr Val Thr Arg Ser Ser Asp Asn Ile Ser Cys Leu Ile Ile Pro Pro
            260                 265                 270
```

```
Leu Leu Val Gln Pro Met Gln Phe Ser Asn Ser Ser Cys Leu Phe Ser
            275                 280                 285

Pro Ser Tyr Asn Ser Thr Glu Glu Ile Asp Leu Gly His Val Ala Phe
        290                 295                 300

Ser Asn Cys Thr Ser Ile Thr Asn Val Thr Gly Pro Ile Cys Ala Val
305                 310                 315                 320

Asn Gly Ser Val Phe Leu Cys Gly Asn Asn Met Ala Tyr Thr Tyr Leu
                325                 330                 335

Pro Thr Asn Trp Thr Gly Leu Cys Val Leu Ala Thr Leu Leu Pro Asp
            340                 345                 350

Ile Asp Ile Ile Pro Gly Asp Glu Pro Val Pro Ile Pro Ala Ile Asp
            355                 360                 365

His Phe Ile Tyr Arg Pro Lys Arg Ala Ile Gln Phe Ile Pro Leu Leu
        370                 375                 380

Ala Gly Leu Gly Ile Thr Ala Ala Phe Thr Thr Gly Ala Thr Gly Leu
385                 390                 395                 400

Gly Val Ser Val Thr Gln Tyr Thr Lys Leu Ser Asn Gln Leu Ile Ser
                405                 410                 415

Asp Val Gln Ile Leu Ser Ser Thr Ile Gln Asp Leu Gln Asp Gln Val
            420                 425                 430

Asp Ser Leu Ala Glu Val Val Leu Gln Asn Arg Arg Gly Leu Asp Leu
        435                 440                 445

Leu Thr Ala Glu Gln Gly Gly Ile Cys Leu Ala Leu Gln Glu Lys Cys
450                 455                 460

Cys Phe Tyr Val Asn Lys Ser Gly Ile Val Arg Asp Lys Ile Lys Thr
465                 470                 475                 480

Leu Gln Glu Glu Leu Glu Arg Arg Lys Asp Leu Ala Ser Asn Pro
                485                 490                 495

Leu Trp Thr Gly Leu Gln Gly Leu Leu Pro Tyr Leu Leu Pro Phe Leu
            500                 505                 510

Gly Pro Leu Leu Thr Leu Leu Leu Leu Thr Ile Gly Pro Cys Ile
        515                 520                 525

Phe Asn Arg Leu Thr Ala Phe Ile Asn Asp Lys Leu Asn Ile Ile His
530                 535                 540

Ala Met
545

<210> SEQ ID NO 4
<211> LENGTH: 562
<212> TYPE: PRT
<213> ORGANISM: Artificial sequence
<220> FEATURE:
<223> OTHER INFORMATION: chimeric envelope glycoprotein in a fusion of
      the transmembrane and extracellular domain of a BaEV envelope
      glycoprotein and the cytoplasmic tail domain of a MLV envelope
      glycoprotein

<400> SEQUENCE: 4

Met Gly Phe Thr Thr Lys Ile Ile Phe Leu Tyr Asn Leu Val Leu Val
1               5                   10                  15

Tyr Ala Gly Phe Asp Asp Pro Arg Lys Ala Ile Glu Leu Val Gln Lys
            20                  25                  30

Arg Tyr Gly Arg Pro Cys Asp Cys Ser Gly Gly Gln Val Ser Glu Pro
        35                  40                  45

Pro Ser Asp Arg Val Ser Gln Val Thr Cys Ser Gly Lys Thr Ala Tyr
    50                  55                  60
```

```
Leu Met Pro Asp Gln Arg Trp Lys Cys Lys Ser Ile Pro Lys Asp Thr
 65              70                  75              80

Ser Pro Ser Gly Pro Leu Gln Glu Cys Pro Cys Asn Ser Tyr Gln Ser
                 85                  90              95

Ser Val His Ser Ser Cys Tyr Thr Ser Tyr Gln Gln Cys Arg Ser Gly
                100                 105             110

Asn Lys Thr Tyr Tyr Thr Ala Thr Leu Leu Lys Thr Gln Thr Gly Gly
            115                 120             125

Thr Ser Asp Val Gln Val Leu Gly Ser Thr Asn Lys Leu Ile Gln Ser
        130             135                 140

Pro Cys Asn Gly Ile Lys Gly Gln Ser Ile Cys Trp Ser Thr Thr Ala
145             150                 155                     160

Pro Ile His Val Ser Asp Gly Gly Pro Leu Asp Thr Thr Arg Ile
                165                 170             175

Lys Ser Val Gln Arg Lys Leu Glu Glu Ile His Lys Ala Leu Tyr Pro
            180                 185             190

Glu Leu Gln Tyr His Pro Leu Ala Ile Pro Lys Val Arg Asp Asn Leu
        195                 200             205

Met Val Asp Ala Gln Thr Leu Asn Ile Leu Asn Ala Thr Tyr Asn Leu
    210                 215                 220

Leu Leu Met Ser Asn Thr Ser Leu Val Asp Asp Cys Trp Leu Cys Leu
225             230                 235                     240

Lys Leu Gly Pro Pro Thr Pro Leu Ala Ile Pro Asn Phe Leu Leu Ser
                245                 250             255

Tyr Val Thr Arg Ser Ser Asp Asn Ile Ser Cys Leu Ile Ile Pro Pro
            260                 265             270

Leu Leu Val Gln Pro Met Gln Phe Ser Asn Ser Ser Cys Leu Phe Ser
        275                 280             285

Pro Ser Tyr Asn Ser Thr Glu Glu Ile Asp Leu Gly His Val Ala Phe
    290                 295             300

Ser Asn Cys Thr Ser Ile Thr Asn Val Thr Gly Pro Ile Cys Ala Val
305             310                 315                     320

Asn Gly Ser Val Phe Leu Cys Gly Asn Asn Met Ala Tyr Thr Tyr Leu
                325                 330             335

Pro Thr Asn Trp Thr Gly Leu Cys Val Leu Ala Thr Leu Leu Pro Asp
            340                 345             350

Ile Asp Ile Ile Pro Gly Asp Glu Pro Val Pro Ile Pro Ala Ile Asp
        355                 360             365

His Phe Ile Tyr Arg Pro Lys Arg Ala Ile Gln Phe Ile Pro Leu Leu
    370                 375             380

Ala Gly Leu Gly Ile Thr Ala Ala Phe Thr Thr Gly Ala Thr Gly Leu
385             390                 395                     400

Gly Val Ser Val Thr Gln Tyr Thr Lys Leu Ser Asn Gln Leu Ile Ser
                405                 410             415

Asp Val Gln Ile Leu Ser Ser Thr Ile Gln Asp Leu Gln Asp Gln Val
            420                 425             430

Asp Ser Leu Ala Glu Val Val Leu Gln Asn Arg Arg Gly Leu Asp Leu
        435                 440             445

Leu Thr Ala Glu Gln Gly Gly Ile Cys Leu Ala Leu Gln Glu Lys Cys
    450                 455             460

Cys Phe Tyr Val Asn Lys Ser Gly Ile Val Arg Asp Lys Ile Lys Thr
465             470                 475                     480
```

-continued

```
Leu Gln Glu Glu Leu Glu Arg Arg Arg Lys Asp Leu Ala Ser Asn Pro
              485                 490                 495

Leu Trp Thr Gly Leu Gln Gly Leu Leu Pro Tyr Leu Leu Pro Phe Leu
            500             505                 510

Gly Pro Leu Leu Thr Leu Leu Leu Leu Thr Ile Gly Pro Cys Ile
        515             520             525

Phe Asn Arg Leu Val Gln Phe Val Lys Asp Arg Ile Ser Val Val Gln
        530             535             540

Ala Leu Val Leu Thr Gln Gln Tyr His Gln Leu Lys Pro Leu Glu Tyr
545             550             555             560

Glu Pro
```